US012195806B2

(12) United States Patent
Stepp et al.

(10) Patent No.: US 12,195,806 B2
(45) Date of Patent: Jan. 14, 2025

(54) P16 POSITIVE TUMOR STRATIFICATION ASSAYS AND METHODS

(71) Applicant: The University of North Carolina at Chapel Hill, Chapel Hill, NC (US)

(72) Inventors: Wesley Hunter Stepp, Carrboro, NC (US); Travis Parke Schrank, Chapel Hill, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 1043 days.

(21) Appl. No.: 17/046,514

(22) PCT Filed: Apr. 12, 2019

(86) PCT No.: PCT/US2019/027273
§ 371 (c)(1),
(2) Date: Oct. 9, 2020

(87) PCT Pub. No.: WO2019/200288
PCT Pub. Date: Oct. 17, 2019

(65) Prior Publication Data
US 2021/0172021 A1    Jun. 10, 2021

Related U.S. Application Data

(60) Provisional application No. 62/656,777, filed on Apr. 12, 2018.

(51) Int. Cl.
C07H 21/02     (2006.01)
C12Q 1/6886    (2018.01)
C12Q 1/70      (2006.01)

(52) U.S. Cl.
CPC .......... *C12Q 1/6886* (2013.01); *C12Q 1/708* (2013.01); *C12Q 2600/106* (2013.01); *C12Q 2600/158* (2013.01)

(58) Field of Classification Search
CPC .............................................. C12Q 2600/158
See application file for complete search history.

(56) References Cited

U.S. PATENT DOCUMENTS

| 2001/0023066 A1 | 9/2001 | Kinders et al. |
| 2006/0188507 A1 | 8/2006 | Georges et al. |
| 2017/0058360 A1 | 3/2017 | Theodorescu et al. |

FOREIGN PATENT DOCUMENTS

WO     2013192089 A1     12/2013

OTHER PUBLICATIONS

Radisky (Cancer Prev Res; 4(12), 2011, 1953-1960).*
Kroemer et al. (Nature Medicine, 21, 10, 2015, 1128-1138).*
Defilippis et al. (American Association for Cancer Discover, 2012, 827-839).*
Frega et al. (Eur. J. Gynaec. Oncol., 2012, 164-167).*
Maufort (Cancer Res; 70(7) Apr. 1, 2010, 2924-2931).*
International Search Report for PCT/US2019/027273, mailed Aug. 19, 2019.
Koifman et al., Proteomics analysis of tissue samples from patients with squamous cell carcinoma of the penis and positive to human papillomavirus. International Brazilian Journal of Urology. Jul.-Aug. 2015, vol. 41, No. 4; p. 642-654.
Parfenov et al., Characterization of HPV and host genome interactions in primary head and neck cancers. Proceedings of the National Academy of Sciences of the U.S.A. Oct. 28, 2014. Epub Oct. 13, 2014, vol. 111. No. 43; p. 1-6; abstract; p. 5, 2nd column, 3rd paragraph; p. 5, 2nd column 4th paragraph; DOI: 10.1073/pnas.1416074111.
Ang et al., "Human Papillomavirus and Survival of Patients with Oropharyngeal Cancer," New England Journal of Medicine, Jul. 2010, vol. 363, pp. 24-35.
Ayers et al., "IFN-γ-related mRNA profile predicts clinical response to PD-1 blockade," Journal of Clinical Investigation, Aug. 2017, vol. 127, No. 8, pp. 2930-2940.
Cancer Genome Atlas Center, "Comprehensive genomic characterization of head and neck squamous cell carcinomas," Nature, Jan. 2015, vol. 517, pp. 576-582.
Cesano et al., "Brining the Next Generation of Immuno-Oncology Biomarkers to the Clinic," Biomedicines, Feb. 2018, vol. 6, No. 14, pp. 1-11.
Chera et al., "Phase 2 Trial of De-intensified Chemoradiation Therapy for Favorable-Risk Human Papillomavirus-Associated Oropharyngeal Squamous Cell Carcinoma," International Journal of Radiation Oncology Biology Physics, Aug. 2015, vol. 93, No. 5, pp. 976-985.
Choby et al., "Transoral Robotic Surgery Alone for Oropharyngeal Cancer: Quality-of-Life Outcomes," JAMA Otolaryngology Head & Neck Surgery, Jun. 2015, vol. 141, No. 6, pp. 499-504.
Danaher et al., "Gene expression markers of Tumor Infiltrating Leukocytes," Journal for Immuno Therapy of Cancer, Feb. 2017, vol. 5, No. 18.
Geiss et al., "Direct multiplexed measurement of gene expression with color-coded probe pairs," Nature Biotechnology, Mar. 2008, vol. 26, No. 3, pp. 317-325.
Gillison et al., "A causal role for human papillomavirus in head and neck cancer," The Lancet, May 2004, vol. 363, No. 9420, pp. 1488-1489.
Gillison, M. L., "Human Papillomavirus-Associated Head and Neck Cancer Is a Distinct Epidemiologic, Clinical, and Molecular Entity," Seminars in Oncology, Dec. 2004, vol. 31, No. 6, pp. 744-754.
Gupta et al., "Local Recurrence in Head and Neck Cancer: Relationship to Radiation Resistance and Signal Transduction," Clinical Cancer Research, Mar. 2002, vol. 8, pp. 885-892.

(Continued)

*Primary Examiner* — Amy Rose Hudson
(74) *Attorney, Agent, or Firm* — Thomas | Horstemeyer, LLP

(57) ABSTRACT

Described herein are assays and methods to detect and/or treat a non-responsive or treatment resistant p16 positive tumor in a subject in need thereof. The disclosed method can also involve determining if the subject is HPV positive or negative, whether the HPV is integrated or episomal, and selecting a suitable treatment based on these determinations. Also disclosed herein is a method of treating an oropharyngeal squamous cell carcinoma in a subject using the arrays and methods disclosed herein.

8 Claims, 28 Drawing Sheets

Specification includes a Sequence Listing.

(56) References Cited

OTHER PUBLICATIONS

Hocking et al., "Head and neck cancer in Australia between 1982 and 2005 show increasing incidence of potentially HPV-associated oropharyngeal cancers," British Journal of Cancer, Feb. 2011, vol. 104, pp. 886-891.
Keck et al., "Integrative Analysis of Head and Neck Cancer Identifies Two Biologically Distinct HPV and Three Non- HPV Subtypes," Clinical Cancer Research, Feb. 2015, vol. 21, No. 4, pp. 870-881.
Lai et al., "Prognostic Significance of p16 Cellular Localization in Oropharyngeal Squamous Cell Carcinoma," Annals of Clinical & Laboratory Science, 2016, vol. 46, No. 2, pp. 132-139.
Layland et al., "The Influence of Lymph Node Metastasis in the Treatment of Squamous Cell Carcinoma of the Oral Cavity, Oropharynx, Larynx, and Hypopharynx: N0 Versus N+," Laryngoscope, Apr. 2005, vol. 115, No. 4, pp. 629-639.
Lewis, Jr. et al., "Human Papillomavirus Testing in Head and Neck Carcinomas: Guideline From the College of American Pathologists," Archives of Pathology & Laboratory Medicine, May 2018, vol. 142, No. 5, pp. 559-597.
Lydiatt et al., "Head and Neck Cancers-Major Changes in the American Joint Committee on Cancer Eighth Edition Cancer Staging Manual," CA: A Cancer Journal for Clinicians, 2017, vol. 67, No. 2, pp. 122-137.
Marur et al., "E1308: Phase II Trial of Induction Chemotherapy Followed by Reduced-Dose Radiation and Weekly Cetuximab in Patients With HPV-Associated Resectable Squamous Cell Carcinoma of the Oropharynx-ECOG- ACRIN Cancer Research Group," Journal of Clinical Oncology, Feb. 2017, vol. 35, No. 5, pp. 490-497.
Mirghani et al., "Human papilloma virus testing in oropharyngeal squamous cell carcinoma: What the clinician should know," Oral Oncology, Jan. 2014, vol. 50, No. 1, pp. 1-9.
Needleman et al., "A General Method Applicable to the Search for Similarities in the Amino Acid Sequence of Two Proteins," Journal of Molecular Biology, Mar. 1970, vol. 48, No. 3, pp. 443-453.
O'Sullivan et al., "Deintensification Candidate Subgroups in Human Papillomavirus-Related Oropharyngeal Cancer According to Minimal Risk of Distant Metastasis," Journal of Clinical Oncology, Feb. 2013, vol. 31, No. 5, pp. 543-550.
Parker et al., "Supervised Risk Predictor of Breast Cancer Based on Intrinsic Subtypes," Journal of Clinical Oncology, Mar. 2009, vol. 27, No. 8, pp. 1160-1167.
Psyrri et al., "The current and future impact of human papillomavirus on treatment of squamous cell carcinoma of the head and neck," Annals of Oncology, Nov. 2014, vol. 25, No. 11, pp. 2101-2115.
Reimers et al., "Combined analysis of HPV-DNA, p16 and EGFR expression to predict prognosis in oropharyngeal cancer," International Journal of Cancer, Apr. 2007, vol. 120, No. 8, pp. 1731-1738.
Rubek et al., "Primary transoral robotic surgery with concurrent neck dissection for early stage oropharyngeal squamous cell carcinoma implemented at a Danish head and neck cancer center: a phase II trial on feasibility and tumour margin status," European Archives of Oto-Rhino-Laryngology, Jan. 2017, vol. 274, pp. 2229-2237.
Shoushtari et al., "Intensity-Modulated Radiotherapy Outcomes for Oropharyngeal Squamous Cell Carcinoma Patients Stratified by p16 Status," Cancer, Jun. 2010, vol. 116, No. 11, pp. 2645-2654.
Steuer et al., "A correlative analysis of PD-L1, PD-1, PD-L2, EGFR, HER2, and HER3 expression in oropharyngeal squamous cell carcinoma," Molecular Cancer Therapeutics, Mar. 2018, vol. 17, No. 3, pp. 710-716.
Wallden et al., "Development and verification of the PAM50-based Prosigna breast cancer gene signature assay," BMC Medical Genomics, Aug. 2015, vol. 8, No. 54., pp. 1-14.
Weinberger et al., "Molecular Classification Identifies a Subset of Human Papillomavirus-Associated Oropharyngeal Cancers With Favorable Prognosis," Journal of Clinical Oncology, Feb. 2006, vol. 24, No. 5, pp. 736-743.
Weinstein et al., "Transoral Robotic Surgery Alone for Oropharyngeal Cancer: An Analysis of Local Control," Archives of Otorhinolaryngology—Head & Neck Surgery, Jul. 2012, vol. 138, No. 7, pp. 628-634.
Zhang et al., "Human papillomavirus (HPV) 16 antibodies at diagnosis of HPV-related oropharyngeal cancer and antibody trajectories after treatment," Oral Oncology, Apr. 2017, vol. 67, pp. 77-82.
Zhao et al., "Different cellular p16INK4a localisation may signal different survival outcomes in head and neck cancer," British Journal of Cancer, Jun. 2012, vol. 107, pp. 482-490.
Zumsteg et al., "Incidence of Oropharyngeal Cancer Among Elderly Patients in the United States," JAMA Oncology, Dec. 2016, vol. 2, No. 12, pp. 1617-1623.

\* cited by examiner

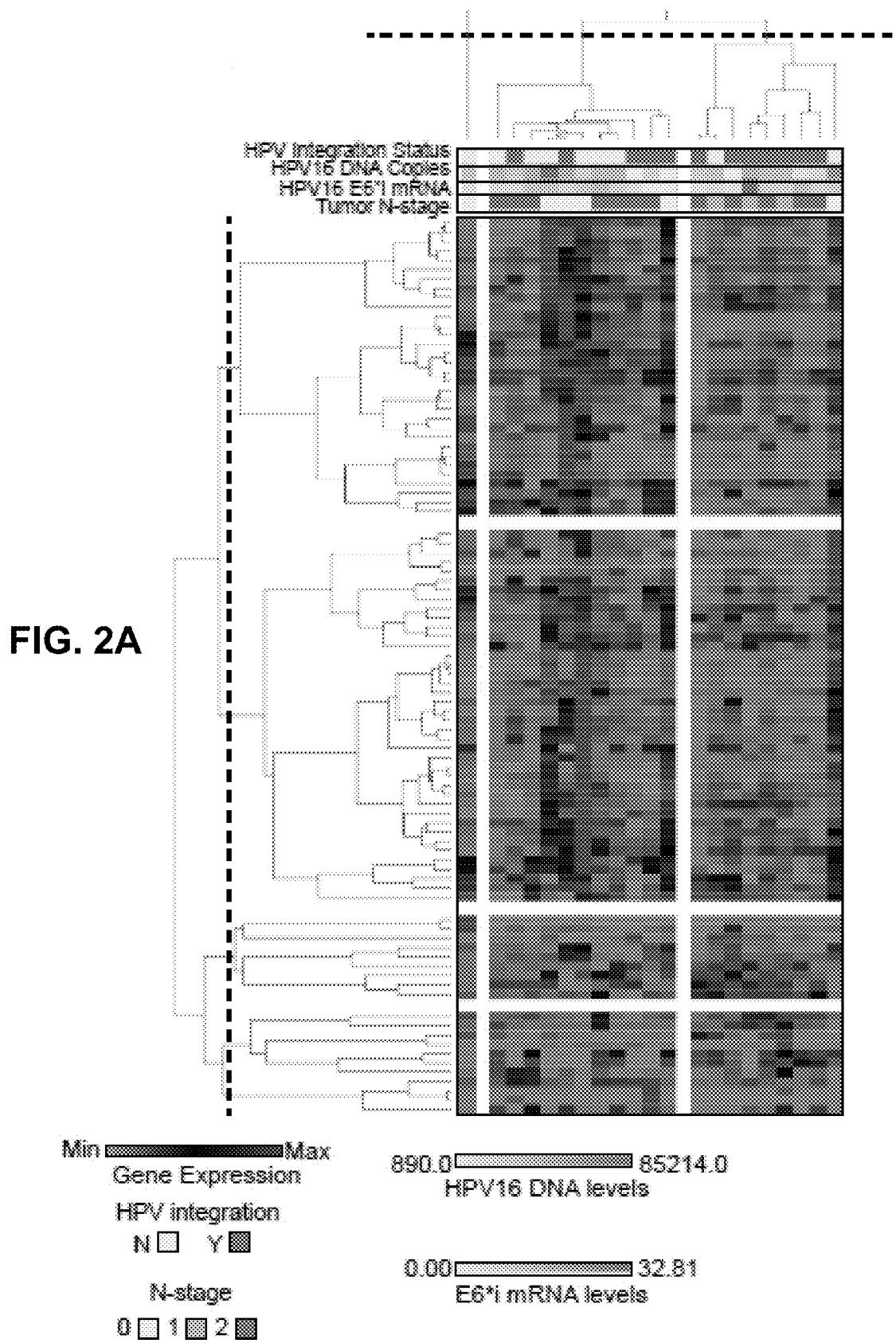

P16 POSITIVE TUMOR STRATIFICATION ASSAYS AND METHODS

CROSS-REFERENCE TO RELATED APPLICATIONS

This invention is a National Stage of International Application No. PCT/US2019/027273, filed Apr. 12, 2019, which claims the benefit of and priority to co-pending U.S. Provisional Patent Application No. 62/656,777, filed on Apr. 12, 2018, entitled "P16 POSITIVE TUMOR STRATIFICATION ASSAYS AND METHODS," the contents of which is incorporated by reference herein in its entirety.

STATEMENT REGARDING FEDERALLY SPONSORED RESEARCH

This invention was made with goverment support under Grant Numbers TR001111 and CA211939 awarded by the National Institutes of Health. The government has certain rights in the invention.

SEQUENCE LISTING

This application contains a sequence listing filed in electronic form as an ASCII.txt file entitled 921404-2040_ST25.txt, created on Apr. 12, 2019. The content of the sequence listing is incorporated herein in its entirety.

BACKGROUND

Oropharyngeal squamous cell carcinoma (OPSCC) is now one of the most common cancers of the upper aerodigestive tract. The risk of developing OPSCC is increased with smoking and/or being infected with human papillomavirus (HPV). Further, patients with Oropharyngeal cancer have an increased risk of developing another caner in the head or neck. OPSCC has an overall 5 year survival rate of about 65%, however the survival rate is greater in people having HPV yet the current standard of care for all is the same. As such there exists a need for improved diagnostic, prognostic, and treatment management strategies for OPSCC.

SUMMARY

Disclosed herein is a method of detecting a non-responsive p16+ cancer tumor in a subject, the method comprising measuring and/or detecting the gene expression of one or more genes selected from the group consisting of: C3, C8G, CCL2, CD36, CD209, CD274, CEACAM1, CMA1, COL3A1, CREB5, CTSG, CX3CL1, CXCL6, CXCL5, DPP4, ENG, F13A1, FLT3LG, FN1, IFITM2, IKBKE, IL1R1, IL1RL1, IL1RN, IL11, IL17RB, IL24, IRF1, ITGA5, ITGB3, JAK2, JAM3, LIF, MME, MS4A2, NT5E, PDGFC, PDGFRB, PRKCD, SIGIRR, SPINK5, TAP1, TAP2, THBS1, THY1, TNFRSF11B, TPSAB1, and any combination thereof. In some embodiments, the method comprises measuring and/or detecting a subset of this list, including any combination of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, or 47 of these genes.

For example, in some embodiments, the method involves measuring and/or detecting C3, CD274, CMA1, CTSG, CX3CL1, ENG, FLT3LG, FN1, IKBKE, IL1R1, IRF1, ITGB3, MME, MS4A2, PDGFC, PRKCD, TAP1, TAP2, THBS1, THY1, and any combination thereof. In some embodiments, the method involves measuring and/or detecting ID274, CMA1, IRF1, MME, TAP1, THY1, and any combination thereof. In some embodiments, the method involves measuring and/or detecting CEACAM1, CD274, IL17RB, CX3CL1, IL1RN, SPINK5, IKBKE, TAP1, SIGIRR, JAK2, IRF1, TNFRSF11B, MS4A2, IL11, IFITM2, ITGB3, JAM3, DPP4, PDGFRB, CREB5, IL1RL1, CCL2, IL1R1, IL24, PDGFC, CD209, LIF, TPSAB1, NT5E, CMA1, C3, THY1, MME, ITGA5, CTSG, F13A1, CXCL6, CXCL5, COL3A1, FN1, C8G, CD36, and any combination thereof. In some embodiments, the method involves measuring and/or detecting CEACAM1, CD274, IL17RB, CX3CL1, IL1RN, SPINK5, IKBKE, TAP1, SIGIRR, JAK2, IRF1, TNFRSF11B, MS4A2, IL11, IFITM2, ITGB3, JAM3, DPP4, PDGFRB, CREB5, IL1RL1, CCL2, IL1R1, IL24, PDGFC, CD209, LIF, TPSAB1, NT5E, CMA1, C3, THY1, MME, ITGA5, CTSG, F13A1, CXCL6, CXCL5, COL3A1, and FN1. In some embodiments, the method involves measuring and/or detecting CEACAM1, CD274, IL17RB, CX3CL1, IL1RN, SPINK5, IKBKE, TAP1, SIGIRR, JAK2, and IRF1. In some embodiments, the method involves measuring and/or detecting TNFRSF11B, MS4A2, IL11, IFITM2, ITGB3, JAM3, DPP4, PDGFRB, CREB5, IL1RL1, CCL2, IL1R1, IL24, PDGFC, CD209, LIF, TPSAB1, NT5E, CMA1, C3, THY1, MME, ITGA5, CTSG, F13A1, CXCL6, CXCL5, COL3A1, and FN1. In some embodiments, the method involves measuring and/or detecting C8G, CD274, CD36, CEACAM1, CMA1, CTSG, DPP4, F13A1, FN1, IRF1, ITGA5, MME, NT5E, TAP1, and THY1. In some embodiments, the method involves measuring and/or detecting C8G, CD274, CD36, CEACAM1, IRF1, and TAP1. In some embodiments, the method involves measuring and/or detecting CD36, CMA1, CTSG, DPP4, F13A1, FN1, ITGA5, MME, NT5E, and THY1. In some embodiments, the method involves measuring and/or detecting CEACAM1, CMA1, CTSG, DPP4, F13A1, FN1, IRF1, ITGA5, MME, NT5E, TAP1, THY1, and CD274.

The disclosed genes can be used to identify a non-responsive p16+ cancer tumor. Therefore, based on the results of the measurement and/or detection, the method can further comprise either treating the subject and/or tumor via a more aggressive treatment method, or treating the subject and/or tumor via a less aggressive treatment method.

The disclosed method can also further include the step of determining if the subject is HPV positive or negative. The disclosed method can also further include the step of determining in an HPV positive subject if the HPV is integrated or episomal. For example, the method can involve measuring the ratio of E6:E5 RNA expression, wherein an elevated E6:E5 ratio is an indication that the HPV is integrated. In these embodiments, the method can also involve treating the subject and/or tumor via a less aggressive method if the subject is HPV positive and the HPV is episomal, and treating the subject and/or tumor via an aggressive method if the subject is HPV positive and the HPV is integrated.

Also disclosed herein is an array comprising a plurality of capture molecules, wherein each capture molecule is each configured to specifically bind a different RNA or a cDNA, wherein each RNA or cDNA corresponds to a different gene selected from the group consisting of: C3, C8G, CCL2, CD36, CD209, CD274, CEACAM1, CMA1, COL3A1, CREB5, CTSG, CX3CL1, CXCL6, CXCL5, DPP4, ENG, F13A1, FLT3LG, FN1, IFITM2, IKBKE, IL1R1, IL1RL1, IL1RN, IL11, IL17RB, IL24, IRF1, ITGA5, ITGB3, JAK2, JAM3, LIF, MME, MS4A2, NT5E, PDGFC, PDGFRB, PRKCD, SIGIRR, SPINK5, TAP1, TAP2, THBS1, THY1, TNFRSF11B, TPSAB1, and any combination thereof. The array can comprise a subset of these genes, including any combination of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, or 47 of these genes.

Therefore, in some embodiments, ach RNA or cDNA corresponds to a different gene selected from the group consisting of: C3, CD274, CMA1, CTSG, CX3CL1, ENG, FLT3LG, FN1, IKBKE, IL1R1, IRF1, ITGB3, MME, MS4A2, PDGFC, PRKCD, TAP1, TAP2, THBS1, THY1, and any combination thereof. In some embodiments, ach RNA or cDNA corresponds to a different gene selected from the group consisting of: C3, CD274, CMA1, CTSG, CX3CL1, ENG, FLT3LG, FN1, IKBKE, IL1R1, IRF1, ITGB3, MME, MS4A2, PDGFC, PRKCD, TAP1, TAP2, THBS1, THY1, and any combination thereof. In some embodiments, ach RNA or cDNA corresponds to a different gene selected from the group consisting of CD274, CMA1, IRF1, MME, TAP1, THY1, and any combination thereof. In some embodiments, ach RNA or cDNA corresponds to a different gene selected from the group consisting of: CEACAM1, CD274, IL17RB, CX3CL1, IL1RN, SPINK5, IKBKE, TAP1, SIGIRR, JAK2, IRF1, TNFRSF11B, MS4A2, IL11, IFITM2, ITGB3, JAM3, DPP4, PDGFRB, CREB5, IL1RL1, CCL2, IL1R1, IL24, PDGFC, CD209, LIF, TPSAB1, NT5E, CMA1, C3, THY1, MME, ITGA5, CTSG, F13A1, CXCL6, CXCL5, COL3A1, FN1, C8G, CD36, and any combination thereof. In some embodiments, ach RNA or cDNA corresponds to a different gene selected from the group consisting of: CEACAM1, CD274, IL17RB, CX3CL1, IL1RN, SPINK5, IKBKE, TAP1, SIGIRR, JAK2, IRF1, TNFRSF11B, MS4A2, IL11, IFITM2, ITGB3, JAM3, DPP4, PDGFRB, CREB5, IL1RL1, CCL2, IL1R1, IL24, PDGFC, CD209, LIF, TPSAB1, NT5E, CMA1, C3, THY1, MME, ITGA5, CTSG, F13A1, CXCL6, CXCL5, COL3A1, and FN1. In some embodiments, ach RNA or cDNA corresponds to a different gene selected from the group consisting of: CEACAM1, CD274, IL17RB, CX3CL1, IL1RN, SPINK5, IKBKE, TAP1, SIGIRR, JAK2, and IRF1. In some embodiments, ach RNA or cDNA corresponds to a different gene selected from the group consisting of: TNFRSF11B, MS4A2, IL11, IFITM2, ITGB3, JAM3, DPP4, PDGFRB, CREB5, IL1RL1, CCL2, IL1R1, IL24, PDGFC, CD209, LIF, TPSAB1, NT5E, CMA1, C3, THY1, MME, ITGA5, CTSG, F13A1, CXCL6, CXCL5, COL3A1, and FN1. In some embodiments, ach RNA or cDNA corresponds to a different gene selected from the group consisting of C8G, CD274, CD36, CEACAM1, CMA1, CTSG, DPP4, F13A1, FN1, IRF1, ITGA5, MME, NT5E, TAP1, and THY1. In some embodiments, ach RNA or cDNA corresponds to a different gene selected from the group consisting of: C8G, CD274, CD36, CEACAM1, IRF1, and TAP1. In some embodiments, ach RNA or cDNA corresponds to a different gene selected from the group consisting of CD36, CMA1, CTSG, DPP4, F13A1, FN1, ITGA5, MME, NT5E, and THY1. In some embodiments, ach RNA or cDNA corresponds to a different gene selected from the group consisting of CEACAM1, CMA1, CTSG, DPP4, F13A1, FN1, IRF1, ITGA5, MME, NT5E, TAP1, THY1, and CD274.

Also disclosed herein is a method of treating an oropharyngeal squamous cell carcinoma in a subject using the arrays and methods disclosed herein. For example, in some embodiments, the oropharyngeal squamous cell carcinoma is a p16 positive oropharyngeal squamous cell carcinoma.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 2A-2B can demonstrate results from unguided hierarchical clustering of differentially expressed genes among N0 and N+ patients reveals gene hot and cold spots. Normalized, linear reads of 164 differentially expressed genes in the NanoString PanCancer Immune Profile RNA assay were uploaded to the Morpheus Analysis Suite as described in FIG. 1. For each sample, integration status (as determined by DNAseq reconstruction using host-HPV-host pairings), HPV DNA copy number (as determined by DNAseq reads for HPV16), viral E6*1 mRNA levels (as determined by qRT-PCR), and AJCC 8, edition N-staging for p16-positive tumors is located at the top of each heat map. FIG. 2A, Samples were processed using a complete linkage, unguided hierarchical clustering based on columns (individual patients) and rows (genes). The patient tree was split at level three (horizontal dashed line), revealing a similar three clusters of patients. The gene tree was split at level three (vertical dashed line), revealing four distinct co-regulated expression "families." FIG. 2B. Clustering for each sample was constrained by degree of nodal involvement. From left to right, patients are clustered as N0, N1 and N2. The inset highlights a distinct cluster of upregulated genes in N0 tumors, or a gene "hot spot."

FIG. 3A. Volcano plot showing differentially expressed genes. Genes that are upregulated fall to the right of the plot and those that are downregulated fall towards the left. Increasing value on the Y-axis corresponds to a higher degree of significance. Dashed lines represent increasing p-value stringency. All genes meeting statistical significance have been highlighted in pink. Genes not achieving significance are represented in gray. FIG. 3Q. Principal component analysis bi-plot showing standardized variance for the two principal components from the top 15 candidate genes for a gene signature. The ovals represent the confidence regions for either N0 (gray) or N+ (orange) tumor samples. Red arrows represent the vector for the identified gene and represents the fit of the line to the 21-sample data set. Each tumor sample is represented by a dot. When samples fall within an oval that matches their color, the test is accurately detecting presence of either N0 or N+ disease.

FIG. 4A. A machine learning gene signature was generated using the top 40 most significant differentially using a linear prediction score (LPS) for N0 or N+ disease based on the formula $\Sigma Xi\beta i$ (where X=log 2 expression level of gene [X] expression level and $\beta$=weighted score based of significance of differential expression). Each tumor is represented as a single dot using Tukey plots, where the median is draw across each box. Whiskers of each plot detail the minimum and maximum values. A two-tailed, unpaired student's t-test was used to determine significance, $CI_{95}$ 8.2-11.13. FIG. 4B. Heat map representing the final gene signature profile of the 40 signature genes identified as predicative of N0 versus N+.

FIG. 6A shows assay without HPV probes. FIG. 6B shows assay with HPV probes.

DETAILED DESCRIPTION

Figure 1:
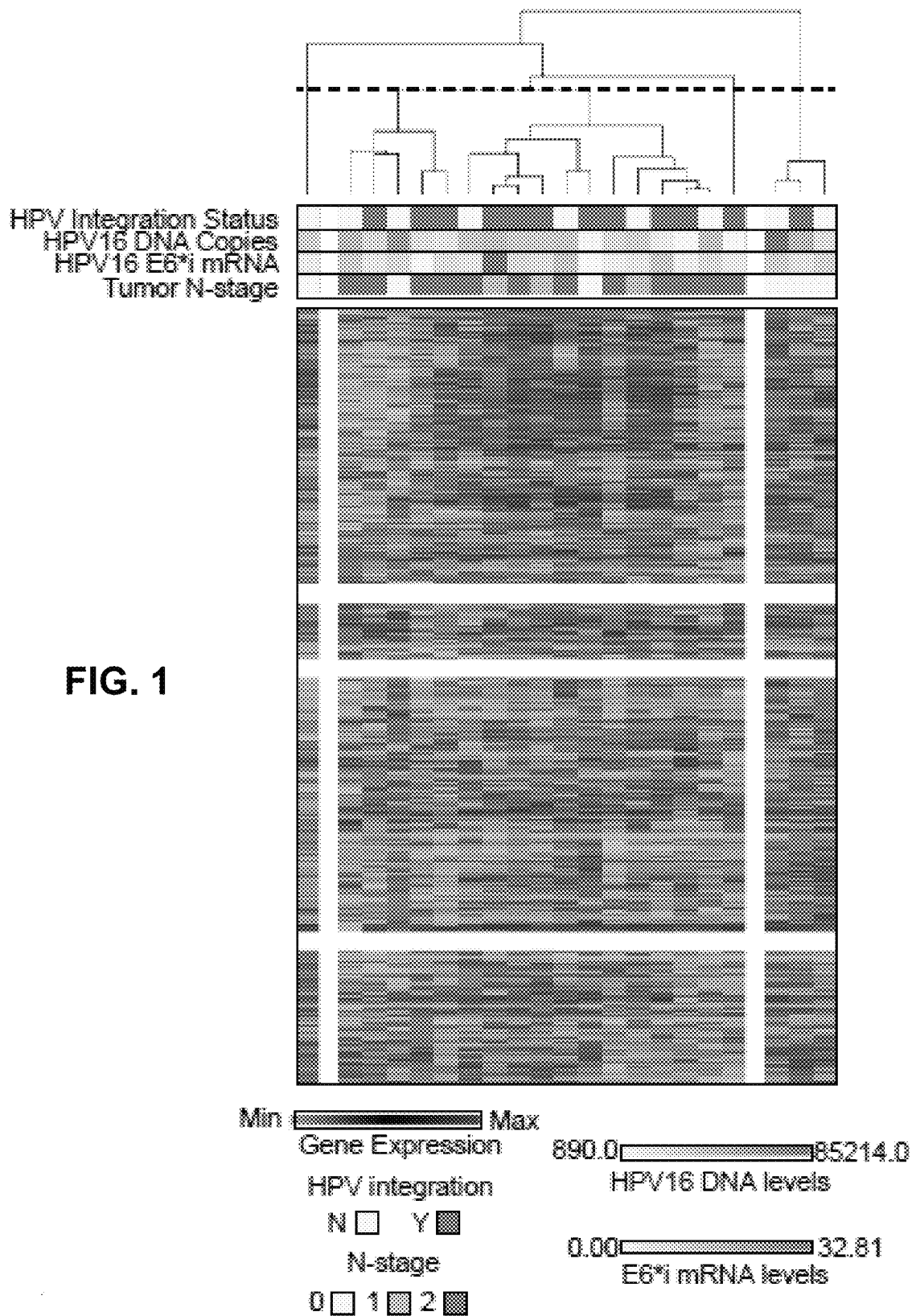
FIG. 1 can demonstrate results from an unguided hierarchical clustering of all patients and all genes reveals grouping bias of N0 and N+ patients. Normalized, linear reads of all 770 genes present in the NanoString PanCancer Immune Profile RNA assay were uploaded to the Morpheus Analysis Suite (software.broadinstitute.org/morpheus/) and were processed using a complete linkage, unguided hierarchical clustering based on columns (individual patients) and rows (genes). The patient sample tree was split at level three (dashed line) to distinguish the most prominent patient groupings. For each sample, integration status (as determined by DNAseq reconstruction using host-HPV-host pairings), HPV DNA copy number (as determined by DNAseq reads for HPV16), viral E6*1 mRNA levels (as determined by qRT-PCR), and AJCC 8th edition N-staging for p16-positive tumors is located at the top of the heat map.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, organic chemistry, biochemistry, physiology, cell biology, cancer biology, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Definitions

As used herein, "about," "approximately," and the like, when used in connection with a numerical variable, can generally refers to the value of the variable and to all values of the variable that are within the experimental error (e.g. within the 95% confidence interval for the mean) or within +/−10% of the indicated value, whichever is greater.

As used herein, "antibody" can refer to a glycoprotein containing at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order FR1, CDR1, FR2, CDR2, FR3, CDR3, and FR4. The variable regions of the heavy and light chains contain a binding domain that interacts with an antigen.

As used herein, "aptamer" can refer to single-stranded DNA or RNA molecules that can bind to pre-selected targets including proteins with high affinity and specificity. Their specificity and characteristics are not directly determined by their primary sequence, but instead by their tertiary structure.

As used herein "attached" as applied to capture molecules of an array refers to a covalent interaction or bond between a molecule on the surface of the support and the capture molecule so as to immobilize the capture molecule on the surface of the support.

As used herein, "capture molecule" refers to a molecule that is configured to specifically bind one or more biomarker molecules of interest. A capture molecule can be a polynucleotide, antibody, antigen, aptamer, affibody, polypeptides, peptides, or combinations thereof that specifically bind one or more biomarkers of interest. For example, the capture molecule can be configured to specifically bind a polynucleotide having at least 5, 10, 15, 20, 30, 40, 50, 60, 70, 80, 90, to 100 or more consecutive nucleotides 90-100% identical to or complementary to a RNA transcript (or corresponding cDNA) transcribed from a gene set forth in any of Tables 1-7 herein.

As used herein, "cDNA" can refer to a DNA sequence that is complementary to a RNA transcript in a cell. It is a man-made molecule. Typically, cDNA is made in vitro by an enzyme called reverse-transcriptase using RNA transcripts as templates.

As used herein with reference to the relationship between DNA, cDNA, cRNA, RNA, protein/peptides, and the like "corresponding to" can refer to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "differentially expressed," can refer to the differential production of RNA, including but not limited to mRNA, tRNA, miRNA, siRNA, snRNA, and piRNA transcribed from a gene or regulatory region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, the term "encode" can refer to principle that DNA can be transcribed into RNA, which can then be translated into amino acid sequences that can form proteins.

As used herein "essentially discrete" as applied to features of an array refers to the situation where 90% or more of the features of an array are not in direct contact with other features of the same array.

As used herein, "expression" can refer to the process by which polynucleotides are transcribed into RNA transcripts. In the context of mRNA and other translated RNA species, "expression" also refers to the process or processes by which the transcribed RNA is subsequently translated into peptides, polypeptides, or proteins. In some instances, "expression" can also be a reflection of the stability of a given RNA. For example, when one measures RNA, depending on the method of detection and/or quantification of the RNA as well as other techniques used in conjunction with RNA detection and/or quantification, it can be that increased/decreased RNA transcript levels are the result of increased/decreased transcription and/or increased/decreased stability and/or degradation of the RNA transcript. One of ordinary skill in the art will appreciate these techniques and the relation "expression" in these various contexts to the underlying biological mechanisms.

As used herein, "gene" can refer to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA.

As used herein, "identity," can refer to a relationship between two or more nucleotide or polypeptide sequences, as determined by comparing the sequences. In the art, "identity" can also refers to the degree of sequence relatedness between nucleotide or polypeptide sequences as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure, unless stated otherwise.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "nucleic acid," "nucleotide sequence," and "polynucleotide" can be used interchangeably herein and can generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. "Polynucleotide", "nucleotide sequences" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotides" as that term is intended herein. As used herein, "nucleic acid sequence" and "oligonucleotide" also encompasses a nucleic acid and polynucleotide as defined elsewhere herein.

As used herein "operatively-linked" as applied to capture molecules of an array refers to a non-covalent interaction between the surface of the support and the capture molecule so as to immobilize the capture molecule on the surface of the support. Such non-covalent interactions include by are not limited to, entrapment by the surface substrate, ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein, "positive control" can refer to a "control" that is designed to produce the desired result, provided that all reagents are functioning properly and that the experiment is properly conducted.

As used herein, "specific binding" can refer to binding which occurs between such paired species such as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins. As another non-limiting example, a miRNA can specifically bind preferably to a miRNA target and not to a non-specific nucleic acid sequence or if binding to a non-specific nucleic acid sequence occurs that no change in the expression or function of the non-specific nucleic acid can be observed or detected. "Specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity.

As used herein, "underexpressed" or "underexpression" can refer to decreased expression level of an RNA (coding or non-coding RNA) or protein product encoded by a gene as compared to the level of expression of the RNA or protein product in a normal or control cell.

Discussion p16 is currently recommend for use as a genetic marker for identifying human papillomavirus positive tumors. In some tumors, such as in the instance of Oropharyngeal squamous cell carcinoma (OPSCC), p16 positive (p16+) tumors (tumors that have elevated expression or overexpress p16) are associated with better outcomes (e.g. improved response to treatment) than those tumors that do not express p16 or do not overexpress p16. Insofar as p16+ tumors appear to be more responsive to treatment, current practice is to de-escalate treatment or exploring primary surgical resection for patients with p16+ malignancy in an attempt to decrease the toxicity profile of current standard of care regimens. Despite overall good outcomes, approximately 10-15% of p16+ tumors have consistently failed treatment, which can be exacerbated in these patients if therapy were de-escalated based only on p16 positivity. Further a tumor's HPV status, and the genomic location of its genome (integrated v. episomal) can affect the severity of the OPSCC.

With that said, described herein are assays and methods that can be used to identify patients with p16+ tumors that are non-responsive to current standard of care treatments and/or are not candidates for specific treatment modalities and/or treatment de-escalation. In some aspects, the assay and/or method can include a step(s) to measure and/or detect gene expression of the group of genes listed in any of Tables 1-9 in a tumor, such as a p16+ tumor, or whether a tumor contains HPV. Further, the assay/method can include determining if the HPV in a tumor is episomal or integrated. Based on the determination if the HPV is episomal or integrated, the treatment applied to the subject can be altered as compared to the current standard of care or that for a p16+ tumor described herein. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

In some aspects, the assay can be configured to measure (qualitatively and/or quantitatively) the gene expression of a group of genes in a tumor sample, such as an OPSCC tumor, that can include or only contain those genes listed in any one of Tables 1-9. Methods of collecting and processing tumor samples are known in the art.

TABLE 1

| 40 Gene Signature Profile | |
|---|---|
| CEACAM1 | IL1RL1 |
| CD274 | CCL2 |
| IL17RB | IL1R1 |
| CX3CL1 | IL24 |
| IL1RN | PDGFC |
| SPINK5 | CD209 |
| IKBKE | LIF |
| TAP1 | TPSAB1 |
| SIGIRR | NT5E |
| JAK2 | CMA1 |
| IRF1 | C3 |
| TNFRSF11B | THY1 |
| MS4A2 | MME |
| IL11 | ITGA5 |
| IFITM2 | CTSG |
| ITGB3 | F13A1 |
| JAM3 | CXCL6 |
| DPP4 | CXCL5 |
| PDGFRB | COL3A1 |
| CREB5 | FN1 |

TABLE 2

Genes of Table 1 Generally Overexpressed in N+ tumors as compared to N0 tumors

| | |
|---|---|
| CEACAM1 | IKBKE |
| CD274 | TAP1 |
| IL17RB | SIGIRR |
| CX3CL1 | JAK2 |
| IL1RN | IRF1 |
| SPINK5 | |

TABLE 3

Genes of Table 1 Generally Underexpressed in N+ tumors as compared to N0 tumors.

| | |
|---|---|
| TNFRSF11B | LIF |
| MS4A2 | TPSAB1 |
| IL11 | NT5E |
| IFITM2 | CMA1 |
| ITGB3 | C3 |
| JAM3 | THY1 |
| DPP4 | MME |
| PDGFRB | ITGA5 |
| CREB5 | CTSG |
| IL1RL1 | F13A1 |
| CCL2 | CXCL6 |
| IL1R1 | CXCL5 |
| IL24 | COL3A1 |
| PDGFC | FN1 |
| CD209 | |

TABLE 4

15 Gene Signature Profile

| | |
|---|---|
| C8G | FN1 |
| CD274 | IRF1 |
| CD36 | ITGA5 |
| CEACAM1 | MME |
| CMA1 | NT5E |
| CTSG | TAP1 |
| DPP4 | THY1 |
| F13A1 | |

TABLE 5

Genes of Table 4 overexpressed in N+ as compared to N0 tumors

| | |
|---|---|
| C8G | IRF1 |
| CD274 | TAP1 |
| CEACAM1 | |

TABLE 6

Genes of Table 4 Underexpressed in N+ as compared to N0 tumors

| | |
|---|---|
| CD36 | FN1 |
| CMA1 | ITGA5 |
| CTSG | MME |
| DPP4 | NT5E |
| F13A1 | THY1 |

TABLE 7

13 Gene Signature Profile

| | |
|---|---|
| CEACAM1 | ITGA5 |
| CMA1 | MME |

TABLE 7-continued

13 Gene Signature Profile

| | |
|---|---|
| CTSG | NT5E |
| DPP4 | TAP1 |
| F13A1 | THY1 |
| FN1 | CD274 |
| IRF1 | |

TABLE 8

20 Gene Signature Profile

| | |
|---|---|
| IRF1 | FLT3LG |
| THBS1 | ENG |
| ITGB3 | TAP2 |
| MME | C3 |
| IL1R1 | TAP1 |
| FN1 | PDGFC |
| MS4A2 | CD274 |
| CMA1 | CX3CL1 |
| CTSG | THY1 |
| PRKCD | IKBKE |

TABLE 9

6 Gene Signature Profile

| | |
|---|---|
| IRF1 | TAP1 |
| MME | CD274 |
| CMA1 | THY1 |

Also described herein are arrays, including, microarrays that can be used to detect and/or measure one or more molecules of interest (biomarkers or target molecules) present in a sample. The sample can be a tumor sample. Methods of collecting tumor samples are known in the art. The arrays can be used to measure the gene expression of one or more genes set forth in Tables 1-9. In some aspects the arrays can be used to detect and/or measure the gene expression of only the genes set forth in any one of Tables 1-9. The biomarkers can be a RNA transcript or cDNA molecule corresponding to an RNA transcript of any of the genes set forth in Tables 1-9. In some aspects the biomarkers (such as an RNA transcript or cDNA molecule corresponding to an RNA transcript) can be only those corresponding to the genes set forth in any one of Tables 1-9. In an array, one or more capture molecules are attached to or operatively linked to a support in essentially discrete locations on the support. The discrete locations on the support where the capture molecule(s) are attached to or operatively linked are individually referred to as a feature of the array and collectively as features. The features can be arranged in any desired arrangement on the support. The arrangement can be such that each feature has its own coordinate so as to allow identification of the capture molecule and/or biomarker detected at any given discrete location in the array according to the coordinate of the feature. These arrays can also be referred to as "ordered arrays". The features can be arranged on the support to be 0.01 nm to 1 cm apart from another feature on the support. A single feature can contain a single capture molecule (singleplex) or can contain more than one capture molecules (multiplex).

The support can be solid or semi-solid. The support can be rigid or be flexible. The support can contain one or more specialized layers that affect the functionality or performance of the array. The support can be two-dimensional or three-dimensional. The support can be made of glass, such as silicon dioxide or borosilicate; plastic, such as polystyrene, nylon, polyvinylidene difluoride; a fibrous material, such as cellulose, carboxy methyl cellulose, or nitrocellulose; a gel, such as agarose, a hydrogel, or polyacrylamide, The support can be formed into any desired shape, including but not limited to a square, a rectangle, a circle, a cube, a rectangular prism, or other regular or irregular polygonal shape or its corresponding three-dimensional shape. The support can have a length, a width, a height, a radius, and/or a diameter. The length of the support can range from about 1 µm to about 10 cm. The height of the support can range from about 1 µm to about 10 cm. The width of the support can range from about 1 µm to about 10 cm. The radius of the support can range from about 1 µm to about 10 cm. The diameter of the support can range from about 1 µm to about 10 cm.

The support can contain a single layer to which the capture molecule is attached or operatively linked. In these embodiments, the support can also be referred to as the surface layer. In other embodiments, the support can contain more than one layer. In embodiments with more than one layer, the layer to which the capture molecule is attached or operatively linked is referred to as the surface layer. The surface layer can be modified to affect the interaction and/or reduce non-specific binding between a capture molecule and the support and/or the capture molecule and the biomarker. In some embodiments, surface layer is modified to enhance the interaction between the capture molecule and the surface layer and/or the interaction between the capture molecule and its corresponding biomarker. The modification of the surface layer can also reduce non-specific binding by the capture molecule and/or the biomarker.

In some embodiments, the surface layer is modified with a chemical modification. Suitable chemical modifications include but are not limited to reactive hydroxide groups, reactive primary, secondary, tertiary, and/or quaternary amine groups, a monolayer of a reactive antibody including but not limited to anti-glutathione S-transferase (anti-GST) antibodies, reactive epoxide groups, reactive methacrylate groups, aldehyde reactive groups, reactive A/G proteins that bind immunoglobulins, and 3-D film coatings, which are polymeric coatings containing activated covalent binding sites. In some embodiments, 3-D film polymeric coatings include, but are not limited to, polysaccharides and hydrophilic polymers. In some embodiments, the 3-D film activated covalent binding sites include, but are not limited to, N-hydroxy succamide esters. The surface layer can be modified to be positively charged, neutral, or negatively charged. The surface layer can be modified to be hydrophilic, hydrophobic, or to contain a mix of hydrophobic and hydrophilic regions. In some embodiments, the modifications are patterned on the surface layer to form discrete functionalized areas to which the capture molecule is attached or operatively-linked. In some embodiments having mixed hydrophobic and hydrophilic regions, the hydrophilic regions are separated by hydrophobic regions. In other embodiments, having mixed hydrophobic and hydrophilic regions, the hydrophobic regions are separated by hydrophilic regions.

In some embodiments, the surface layer is a gel, including but not limited to agarose, a hydrogel, or polyacrylamide. In some embodiments the support contains multiple discrete gel surface layers. These gel surface layers are also referred to as pads and can be arranged on the support in an ordered arrangement such that each gel pad is a feature of the array. In some embodiments, the same capture molecule(s) are attached to or operatively linked to all the gel pads forming the surface layer of the support. In other embodiments, at least two of the gel pads have at least one different capture molecule attached or operatively linked thereto.

The support can be configured to have one or more three dimensional discrete indentations or depressions in the surface layer. The capture molecule(s) can be attached or operatively linked to the indentation. The three dimensional indentions can be square, rectangular, round, or irregular shaped. The three dimensional indentations can form wells or channels. One or more indentations can be connected to another indentation by a three dimensional connector channel extending between the one or more wells. In some embodiments, the connector channel is a microfluidic channel. In some embodiments, the microfluidic channel contains wicking paper. A dimension of the indentation can range from about 1 µm to about 10 cm. In some embodiments, a length of an indentation ranges from about 1 µm to about 10 cm. In further embodiments, a width of an indentation can range from about 1 µm to about 10 cm. In additional embodiments, a height of an indentation can range from about 1 µm to about 10 cm. In other embodiments, the radius of an indentation can range from about 1 µm to about 10 cm. In further embodiments, the diameter of an indentation can range from about 1 µm to about 10 cm. The indentations can be so dimensioned so as to hold a specific volume. In some embodiments, the specific volume can range from about 1 nL to about 1,000 mL. In a single array, the indentations can all be about the same dimension. In other embodiments, at least two of the indentations differ in at least one dimension. Any surface of an indentation can be modified as described above with respect to modification of the surface layer.

The support can also contain additional layers beneath the surface layer and within the support. The additional layers can be directly beneath the surface layer or contain other layers, such as the support, between the additional layer and the surface layer. The additional layer can improve the signal to noise ratio, affect signal production produced by the binding of a capture molecule to a biomarker or other substrate, and affect other properties or performance parameters of the array. In some embodiments the additional layer is a dielectric layer. The dielectric layer can improve the reflection of the signal produced upon binding of a capture molecule and a biomarker.

In some aspects, the biomarkers can be detected by another assay or method including, any sequencing method (including traditional methods (e.g. Sanger sequencing) and next generation sequencing methods (e.g. pyrosequencing, proton/PGM sequencing, SOUD sequencing, Illumina (Solexa) sequencing, massively parallel signature sequencing), any suitable PCR method (e.g. RT-PCR, qPCR, RT-qPCR, RNA sequencing, Northern blotting, and in situ hybridization). These methods can be single or multiplexed.

After a suitable method is used to measure and/or detect the expression of the desired gene(s), the expression can be quantified. In some aspects, the expression levels in the sample can be compared to one or more suitable controls to determine if expression is elevated or reduced. In some aspects, the control can be a reference sample, a N0 tumor, and/or a N+ tumor.

In aspects, the method can involve assaying a biological sample, such a tissue sample and/or tumor tissue sample, from the subject for the expression levels of HPV viral RNAs, p16-mRNA expression and/or any combination of genes as set forth in Tables 1-9, comparing the gene expression levels of HPV viral RNA levels, p16 expression levels and/or any combination of genes as set forth in Tables 1-9 to values of a suitable control to produce a gene expression profile; and analyzing the gene expression profile to calculate a nodal status. A patient treatment strategy can be determined and implemented based on the nodal status of the tumor as discussed elsewhere herein.

A nodal score can be determined using standard statistical methods, such as multivariate analysis. In some embodiments, the nodal status is a regression value. For example, the gene expression profile may be analyzed by multivariate regression analysis (e.g., determined by linear regression) or principal component analysis to derive a nodal status. In other aspects, specific gene expression biomarkers (e.g. those genes discussed with respect to Tables 1-9) are used to calculate the nodal status. For example, in some aspects, levels of p16 expression, HPV viral RNA expression and/or any of the genes described in Tables 1-9 relative to values of a suitable control can be negatively or positively correlated to nodal status as described elsewhere herein.

In some aspects, the gene expression of p16, HPV viral RNAs and/or one or more genes discussed in relation to Tables 1-9 can be used to derive a nodal status that predicts the likelihood that a treatment will be successful and/or necessary and/or determine that a treatment is effective or not. In some aspects, the gene expression of p16, HPV viral RNAs and/or one or more genes discussed in relation to Tables 1-9 can be used to derive a nodal status that determines the stage and/or prognosis of the disease. In some embodiments, the gene expression profile contains numerous data points that are best managed and stored in a computer readable form. Therefore, in some aspects, the nodal status is a regression value derived from the gene expression profile as a weighted function of the quantified gene expression profile. The weighted function can be derived from linear regression analysis of experimental results comparing gene expression of tissue normal subjects or normal tissue form the subject treated versus those with OSCC or from OSCC tumor tissue from the subject to be treated (autologous tumor tissue) or tumor tissue from one or more other subjects (allogeneic tumor tissue). Each gene expression species can be multiplied by a weighting constant and summed.

Generally speaking, a regression value is a single value that is sensitive to changes in abundance of gene species of a gene expression profile, with a regression value of about 1 being indicative of a high association or correlation with the same phenotypic response or indicative of being involved in and/or contributing to the same phenotypic response.

After detection and/or measurement of the gene expression in the sample, the tumor and/or subject can be treated. In some aspects, treatment of a subject and/or tumor that is determined based on an assay described herein to be a N+ tumor, can include more aggressive methods. In some aspects, treatment of a subject and/or tumor that is determined based on an assay described herein to be a N0 tumor can include less aggressive methods.

Prior to analysis, the data in each dataset can be collected by measuring the values for each gene biomarker, usually in duplicate or triplicate or in multiple replicates. The data may be manipulated, for example raw data may be transformed using standard curves, and the average of replicate measurements used to calculate the average and standard deviation for each patient. These values may be transformed before being used in the models, e.g. log-transformed, Box-Cox transformed, etc. This data can then be input into an analytical process with defined parameter.

The analytic nodal classification process may be any type of learning algorithm with defined parameters, or in other words, a predictive model. In general, the analytical process will be in the form of a model generated by a statistical analytical method such as those described below. Examples of such analytical processes may include a linear algorithm, a quadratic algorithm, a polynomial algorithm, a decision tree algorithm, or a voting algorithm.

Using any suitable learning algorithm, an appropriate reference or training dataset can be used to determine the parameters of the analytical process to be used for classification, i.e., develop a predictive model. The reference or training dataset to be used will depend on the desired classification to be determined. The dataset may include data from two, three, four or more classes.

The number of features that may be used by an analytical process to classify a test subject with adequate certainty is 2 or more. In some embodiments, it is 3 or more, 4 or more, 10 or more, or between 10 and 200. Depending on the degree of certainty sought, however, the number of features used in an analytical process can be more or less, but in all cases is at least 2. In one embodiment, the number of features that may be used by an analytical process to classify a test subject is optimized to allow a classification of an OSCC tumor of a test subject with high certainty.

Suitable data analysis algorithms are known in the art. In one embodiment, a data analysis algorithm of the disclosure comprises Classification and Regression Tree (CART), Multiple Additive Regression Tree (MART), Prediction Analysis for Microarrays (PAM), or Random Forest analysis. Such algorithms classify complex spectra from biological materials, such as a blood, tissue (e.g. tumor tissue) sample, to distinguish the nodal status of the OSCC tumor. In other embodiments, a data analysis algorithm of the disclosure comprises ANOVA and nonparametric equivalents, linear discriminant analysis, logistic regression analysis, nearest neighbor classifier analysis, neural networks, principal component analysis, hierarchical cluster analysis, quadratic discriminant analysis, regression classifiers and support vector machines.

As will be appreciated by those of skill in the art, a number of quantitative criteria can be used to communicate the performance of the comparisons made between a test marker profile and reference marker profiles. These include area under the curve (AUC), hazard ratio (HR), relative risk (RR), reclassification, positive predictive value (PPV), negative predictive value (NPV), accuracy, sensitivity and specificity, Net reclassification Index, Clinical Net reclassification Index. In addition, other constructs such a receiver operator curves (ROC) can be used to evaluate analytical process performance.

The method can also include determining if the HPV, if present, is episomal or integrated. Patients with HPV integration have a much stronger oncogenic drive, as HPV integrates in the E2 region of the viral genome. This results in uncontrolled expression of the oncoproteins. E6 and E7, which results in a higher degree of malignant transformation and a more aggressive disease. The method of determining if HPV is integrated or episomal can include measuring the ratio of E6:E5 RNA expression. In these embodiments, an elevated E6:E5 ratio is an indication that the HPV is integrated. In some cases, the higher the E6:E5 ratio, the high probability that the HPV is integrated. For example, a ratio of E6:E5 greater than 1:1, such as at least 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20, can be an indication that the HPV is integrated. E5 and E6 RNA expression can be detected using known methods. In some cases, RNA expression is measured using oligonucleotide probes. For example the following oligonucleotides can be used as probes to detect E5a and E6 RNA:

```
                                    (E5a, SEQ ID NO: 5)
TACTGCATCCACAACATTACTGGCGTGCTTTTTGCTTTGCTTTTGTGTGCT

TTTGTGTGTCTGCCTATTAATACGTCCGCTGCTTTTGTCTGTGTCTACA;
and (E6, SEQ ID NO: 6)
GAATGTGTGTACTGCAAGCAACAGTTACTGCGACGTGAGGTATATGACTTT

GCTTTTCGGGATTTATGCATAGTATATAGAGATGGGAATCCATATGCTG.
```

Knowing whether or not a patient is a) HPV-positive and b) if they are HPV-positive, whether the viral genome is episomal or integrated changes the treatment strategy and subsequent treatment regimen of the subject as compared to the current "standard of care". In short, clinical decision making and treatment options can be expanded or limit the scope of therapies that are considered the "standard of care" for a specific patient based on determining if the patient is HPV positive and if their tumor has viral genome that is episomal or integrated.

HPV-negative patients can receive maximum therapy, including surgical resection, chemotherapy, and radiotherapy at the highest doses. HPV-positive patients can be eligible for a less aggressive approach that can include primary radiotherapy alone (e.g. reduced side effect profiles from treatment), and certain patient cohorts with minimally invasive or aggressive disease may be eligible for further reduced-dose radiotherapy (e.g. even less side effects from treatment). However, patients with integrated HPV disease, do not benefit from reduced radiotherapy treatment and their disease course tracks more like that of an HPV-negative patient. As such, even if the patient is HPV positive they may need and can be eligible for a more aggressive therapy approach similar or the same as that applied to an HPV-negative patient.

Also provided herein are methods of treating a head or neck cancer in a subject in need thereof, where the method can include detection and/or measurement of the gene expression of a group of genes as set forth in any of Tables 1-9 as described elsewhere herein. In some aspects the cancer is an oropharyngeal squamous cell carcinoma. In some aspects, the cancer is a p16+ cancer. In some aspects, the cancer is an OPSCC p16+ cancer. In some aspects, the subject in need thereof has HPV that is integrated. In some aspects, the subject in need thereof has HPV that is episomal.

After the step of detection and/or measurement of gene expression described above, the subject can be treated based on the tumor nodal status and/or if the HPV is episomal or integrated. Specific treatment regimens based on OPSCC tumor nodal status and/or HPV status (episomal or integrated) are discussed elsewhere herein.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction.

Oropharyngeal squamous cell carcinoma (OPSCC) is now one of the most common cancers of the upper aerodigestive tract, and the rising incidence can primarily be attributed to human papillomavirus (HPV) infection (Ang K K, et al. N Engl J Med. 2010 363(1):24-35; Hocking J S. et al. Br J Cancer. 2011 104(5):886-891; Zumsteg Z S. et al. JAMA Oncol. 2016 2(12):1617-1623). HPV-driven OPSCC is an epidemiologically and molecularly distinct subset of oropharyngeal cancer (Gillison M L. Semin Oncol. 2004 31(6):744-754; Gillison M L, et al. Lancet. 2004 363(9420): 1488-1489). It is associated with the overexpression of the tumor suppressor protein p16 and has markedly better outcomes than non-HPV driven OPSCC (Reimers N, et al. Int J Cancer. 2007 120(8):1731-1738; Shoushtari A, et al. Cancer. 2010 116(11):2645-2654: Weinberger P M, et al. J Clin Oncol. 2006 24(5):736-747). The HPV oncoproteins E6 and E7 mediate the degradation of the cellular checkpoint proteins p53 and pRB, respectively. The degradation of pRB by E7 results in unregulated p16 expression and has led to the correlation of elevated p16 expression with HPV-positive tumors. This, combined with the ease and inexpensive nature of p16 testing, have led many to recommend the use of p16 expression as a surrogate marker for HPV-positivity in OPSCC (Psyrri A, et al. Ann Oncol. 2014 25(11):2101-2115; Lai S, et al. Ann Clin Lab Sci. 2016 46(2):132-139; Zhao N, et al. Br J Cancer. 2012 107(3):482-490).

Since HPV-driven OPSCC is associated with markedly better outcomes, multiple trials have been conducted exploring either primary surgical resection or RT de-escalation for patients with p16+ malignancy in an attempt to decrease the toxicity profile of current standard of care regimens (Chera B S, et al. Int J Radiat Oncol Biol Phys. 2015 93(5):976-985; Rubek N, et al. Eur Arch Otorhinolaryngol. 2017 274(5): 2229-2237). Despite overall good outcomes, approximately 10-15% of p16+ tumors have consistently failed radiotherapy (O'Sullivan B. et al. J Clin Oncol. 2013 31(5):543-550), which may stem from radiation resistance pathways (Gupta A K, et al. Clin Cancer Res. 2002 8(3):885-892) or misdiagnosis of HPV-driven disease, possibly reflecting molecular heterogeneity among p16-positive tumors that is not well understood (Vermeer D W, et al. Oncotarget. 2016 7(17):24194-24207). Additionally, several studies have demonstrated that primary transoral robotic surgery is effective in select patient groups, suggesting that a diagnostic for risk-stratifying patients for different treatment modalities could be useful (Rubek N, et al. Eur Arch Otorhinolaryngol. 2017 274(5):2229-2237; Choby G W, et al. JAMA Otolaryngol Head Neck Surg. 2015 141(6):499-504; Weinstein G S, et al. Arch Otolaryngol Head Neck Surg. 2012 138(7): 628-634). Thus, while p16 staining in OPSCC biopsies has a very high sensitivity for detecting HPV-positive disease, its specificity is a major drawback (Mirghani H, et al. Oral Oncol. 2014 50(1):1-9).

Dependence of treatment decisions on p16 staining alone may also lead to false identification of a purely HPV driven process (Lewis J S, et al. Arch Pathol Lab Med. 2017). For instance, elevated p16 expression can be seen outside of HPV+ disease, such as in HPV-negative OPSCC tumors (Zhao N, et al. Br J Cancer. 2012 107(3):482-490) and adenoid cystic carcinoma of the trachea (Chera B S, et al. Int J Radiat Oncol Biol Phys. 2015 93(5):976-985). The prognostic significance of p16 overexpression alone in OPSCC has been documented (Ang K K, et al. N Engl J Med. 2010 363(1):24-35; Shoushtari A, et al. Cancer. 2010 116(11): 2645-2654; Rubek N, et al. Eur Arch Otorhinolaryngol. 2017 274(5):2229-2237; O'Sullivan B, et al. J Clin Oncol. 2013 31(5):543-550); however, aberrant p16 expression in carcinogen-driven (i.e. HPV-negative) and in non-HPV16 tumors harboring other HPV types[15] highlights the need for higher specificity, especially when one considers up and coming modifications to standard of care regiments, such as RT de-intensification. Further, the ability to successfully identify more aggressive p16+ tumor subtypes pre-treatment may lead to treatment escalation and avoidance of recurrence due to improper de-intensification.

Presently, there is not a diagnostic molecular biomarker available that utilizes both tumor RNA genetics and HPV viral RNA expression to detect p16+ OPSCCs subtypes. The identification of tumor-specific prognostic gene expression signatures at initial clinical staging could aid in the selection of a directed, patient-specific treatment modality, identify which patients are at risk for recurrent disease or predict occult LN involvement, which is present in 20% of all OPSCCs (Layland M K, et al. Laryngoscope. 2005 115(4): 629-639). Further, knowing a tumor's likelihood to fail RT de-intensification at initial clinical staging or following surgery could aid surgical and medical management both pre- and post-operatively.

In this Example, gene expression levels of 770 oncologic or immunoregulatory genes in banked OPSCC tumor samples were analyzed and combined the resulting data with DNA sequencing reads for HPV DNA and E6/E7 mRNA expression to identify unique onco-immune phenotypes in p16-positive patients with either N0, N1 or N2 disease according to AJCC $8^{th}$ edition nodal criteria (Lydiatt W M, et al. C A Cancer J Clin. 2017 67(2):122-137). Key tumor gene expression changes can vary by degree of LN involvement and thereby this Example can demonstrate, among other things, development of a tumor immunophenotype by nodal status.

Methods.

Biospecimen identification and procurement. Informed consent was obtained from patients who were treated for oropharyngeal squamous cell carcinoma and the tissue was collected and stored under the Lineberger Comprehensive Cancer Care Center (LCCC) UNCseq initiative. Using a secondary approved protocol, 15-1604, banked fresh-frozen paraffin embedded (FFPE) tumor tissue was procured from 21 of 48 total banked cases with a diagnosis of OPSCC, confirmed p16+ immunohistochemistry and HPV16 positive DNA status. The 21 OPSCC cases with primary site biopsy were selected according to tumor block availability. Fourteen cases were excluded due to insufficient tumor available, along with three additional cases that were found to be non-HPV16 genotype. Tumor blocks were sectioned into five 10-μm sections by the Tissue Pathology Core Facility at UNC LCCC and FFPE sections and were then placed onto glass slides. For each tumor, one hematoxylin and eosin (H/E) slide was prepared prior to nucleic acid harvest, analyzed and marked by a board-certified pathologist to identify the tumor from non-tumor prior to macro-dissection of each sample.

Clinical Data Elements. Clinical data were collected for all specimens and included primary OP subsite, gender, age at diagnosis, race, ethnicity, tumor grade, smoking history, and HPV status. Tumor, Node, and Metastasis (TNM) staging components were confirmed for all cases in the study. A compiled tumor stage using the standard AJCC $8^{th}$ edition staging criteria for TNM was reported as identified by radiographic assessment. Clinical and vital (living/deceased) status as well as tumor status of patients was also recorded. Recurrence was calculated as the number of months to a new tumor event using a no-recurrence cutoff of 36 months. Smoking status was coded as a binary term. Patients who were reported as lifelong nonsmokers were termed "never smokers." and all other subjects were considered smokers. For patients who received RT, or combination chemo-RT (CRT), definitive RT was considered 66-70 Gy.

RNA isolation and quality assessment. All RNA was extracted from FFPE samples where tumor tissue was macrodissected and resulting samples were extracted using a Maxwell RSC automated extractor (Promega) with Maxwell RSC RNA FFPE kits. RNA was analyzed prior to NanoString preparation work flow to determine RNA quality and fragment size using a standard RNA Screentape/Tapestation Assessment (Agilent Technologies). Prior to sample hybridization, RNA quantitation was determined using Qubit 3.0 nucleic acid fluorimeter (Life Technologies) with a Qubit 3.0 RNA Hi-Sensitivity analysis kit (Life Technologies).

Gene expression assays. Validation of mRNA transcripts was performed using nCounter assays. 50 ng of purified RNA was hybridized to target specific probes as has been previously described (Geiss G K, et al. Nat Biotechnol. 2008 26(3):317-325) using the commercially available PanCancer Immune Profile CodeSets (NanoString Technologies), which contains 730 target genes and 40 "housekeeping" genes. Counts for each RNA species were extracted and analyzed using NSolver v.3.0 software provided by Nanostring™.

Viral qRT-PCR

Reverse transcription reactions were performed with the Transcriptor First-Strand Synthesis kit (Roche AG; Mannheim, Germany) using 1 μg of total RNA, 60 μM random hexamers, and 2.5 μM oligo-dT primers and expression of the indicated genes was analyzed by qPCR using a QuantStudio 6 Flex Real Time PCR System (Applied Biosystems; Forest City, Calif.) using SYBR green PCR master mix (Roche AG; Mannheim, Germany). Each reaction mixture contained 1×SYBR green master mix, cDNA from 1 μg of RNA, and 0.3 μM each oligonucleotide primer in a total volume of 20 μl. Primers for E6*1 (E6/E7) were as follows: 5'-CAAGACAGTATTGGAACTTACAGAGGTG-'3 (sense) (SEQ ID NO: 1) and 5'-CTGGCCTC-TATAGTGCCCAGC-'3 (antisense) (SEQ ID NO: 2). All values were normalized the levels of TATA-binding protein (TBP) using the following primers: 5'-TAAACTTGACCTAAAGACCATTGCA-'3 (sense) (SEQ ID NO: 3) and 5'-CAGCAAACCGCTTGGGATTA-'3 (antisense) (SEQ ID NO: 4).

Data and statistical analysis. For all patient demographics, descriptive statistics were used to compare the demographic, stage, treatment and outcomes between node-positive and node-negative patients. Fischer exact tests were used for categorical variables, t-tests were used for continuous variables, Wilcoxon-Mann-Whitney tests were used for non-normally distributed variables, and log-rank tests were used to determine recurrence and survival.

RNA expression data generated by NanoString was normalized using the nSolver analysis software and, where indicated in figure legends, log 2 transformed. For heat map presentation and data clustering, Morpheus (a web-based data analysis tool) was utilized (https://software.broadinstitute.org/morpheus). Data clustering was accomplished using unguided, hierarchical clustering with complete linkage.

Graphs and statistical analyses were generate using Prism 7 (GraphPad Software) and two-tailed student t-tests, unless otherwise specified. A gene signature was obtained either by principal component analysis using the 2:1 ratio of upregulated to downregulated genes in LN negative tumors or by a machine learning program based on a linear predictor score (LPS) equation (Ayers M, et al. J Clin Invest. 2017 127(8):2930-2940: Cesano A, et al. Biomedicines. 2018 6(1); Danaher P, et al. J Immunother Cancer. 2017 5:18), $\Sigma Xi\beta i$, where X is equal to gene [X] expression level and P is equal to a gene's weighted valued based on its significance. A test set of ROC curves were generated by a machine learning program based on the LPS algorithm. The training data sets were split randomly into selected test sets to perform cross validation. A total of 500 cross validation tests were performed to generate the mean AUC. Data analysis services were contracted by NanoString Technologies for thorough computational and statistical analysis of our genetic signature model.

Results

Demographics. A total of 48 patients with prospectively collected p16-positive OPSCC samples as part of the UNCSeq cohort were retrospectively analyzed for several clinical variables including: age, gender, race, p16 status, HPV status, smoking status and pack year history. RT history, average RT dose, mortality, incidence of recurrence, and disease-free survival (DFS). In total, 21 patients (mean [SD] age, 54.6 [9.6] years; 18 [85.7%] males and three [14.3%] females) with confirmed p16-positive IHC and HPV16 genotype OPSCC were included in the final analysis, gives the demographic and clinical characteristics of all the patients with molecular analysis included in this study, stratified by radiographic lymph node staging.

TABLE 10

Demographics and clinical characteristic of patients stratified by nodal status

| Parameter | Node-negative (n = 6) N | % | Node-positive (n = 15) N | % | Total (n = 21) N | % | p-Value |
|---|---|---|---|---|---|---|---|
| Age Category | | | | | | | |
| 30-40 (n = 1) | 1 | 17% | 0 | 0% | 1 | 5% | 0.781*^ |
| 40-50 (n = 7) | 2 | 33% | 5 | 33% | 7 | 33% | |
| 50-60 (n = 6) | 0 | 0% | 6 | 40% | 6 | 29% | |
| 60-70 (n = 6) | 3 | 50% | 3 | 20% | 6 | 29% | |
| 70+ (n = 1) | 0 | 0% | 1 | 7% | 1 | 5% | |
| Total (n = 21) | 6 | 100% | 15 | 100% | 21 | 100% | |
| Gender | | | | | | | |
| Male (n = 18) | 6 | 100% | 12 | 80% | 18 | 86% | 0.526& |
| Female (n = 3) | 0 | 0% | 3 | 20% | 3 | 14% | |
| Smoking Status | | | | | | | |
| Non-Smoker (n = 9) | 2 | 33% | 7 | 47% | 9 | 43% | 0.659& |
| Smoker (n = 12) | 4 | 67% | 8 | 53% | 12 | 57% | |
| Pack Years | | | | | | | |
| <10 (n = 4) | 0 | 0% | 4 | 50% | 4 | 33% | 0.208& |
| 10+ (n = 8) | 4 | 100% | 4 | 50% | 8 | 67% | |
| Nodal Status | | | | | | | |
| N0 (n = 6) | 6 | 100% | 0 | 0% | 6 | 29% | |
| N1 (n = 3) | 0 | 0% | 3 | 20% | 3 | 14% | |
| N2 (n = 12) | 0 | 0% | 12 | 80% | 12 | 57% | |
| HPV Integration | | | | | | | |
| Non-integrated (n = 9) | 4 | 67% | 5 | 33% | 9 | 43% | 0.331& |
| Integrated (n = 12) | 2 | 33% | 10 | 67% | 12 | 57% | |
| Total (n = 21) | 6 | 100% | 15 | 100% | 21 | 100% | |
| Treatment | | | | | | | |
| Surgery Alone (n = 4) | 2 | 33% | 2 | 13% | 4 | 19% | 0.146**& |
| Surgery with Adj. RT (n = 2) | 2 | 33% | 0 | 0% | 2 | 10% | |
| Surgery with Adj. CRT (n = 2) | 0 | 0% | 2 | 13% | 2 | 10% | |
| Radiation Alone (n = 2) | 1 | 17% | 1 | 7% | 2 | 10% | 0.146& |
| Chemoradiation (n = 11) | 1 | 17% | 10 | 67% | 11 | 52% | 0.544& |

TABLE 10-continued

Demographics and clinical characteristic of patients stratified by nodal status

| Parameter | Node-negative (n = 6) | | Node-positive (n = 15) | | Total (n = 21) | | p-Value |
|---|---|---|---|---|---|---|---|
| | N | % | N | % | N | % | |
| Radiation Dosage | | | | | | | |
| 60 GY@ (n = 10) | 2 | 50% | 8 | 62% | 10 | 59% | >0.99& |
| 66 GY (n = 2) | 1 | 25% | 1 | 8% | 2 | 12% | 0.426& |
| 70 GY (n = 5) | 1 | 25% | 4 | 31% | 5 | 29% | >0.99& |

@Denotes de-intensified dose;
*p-value for difference in mean age;
**p-value for primary surgical vs. non-surgical treatment;
^student's t-test;
&Fischer's exact test Nanostring tumor RNA profiling. RNA was isolated from FFPE OPSSC samples and performed medium-throughput gene expression analysis using NanoString RNA assays to determine if a tumor's gene expression profile would be predictive of a known clinical correlate of outcomes such as LN involvement. Following unguided hierarchical clustering of all 770 genes in the array, we found that patients with no nodal involvement typically clustered in the same clade, compared to those with any LN involvement (N1 or N2) (FIG. 1). This was independent of overall HPV DNA copy number, E6/E7 mRNA expression, or HPV integration status (FIG. 1). Further, there was no significant difference between E6/E7 expression levels ($C_{95}$ (−5.092) to 9.23) HPV16 DNA copies ($CI_{95}$(−35053.0) to 4858.0), or viral integration status when comparing N0 versus N+ tumors (Table 10).

Figure 2B:
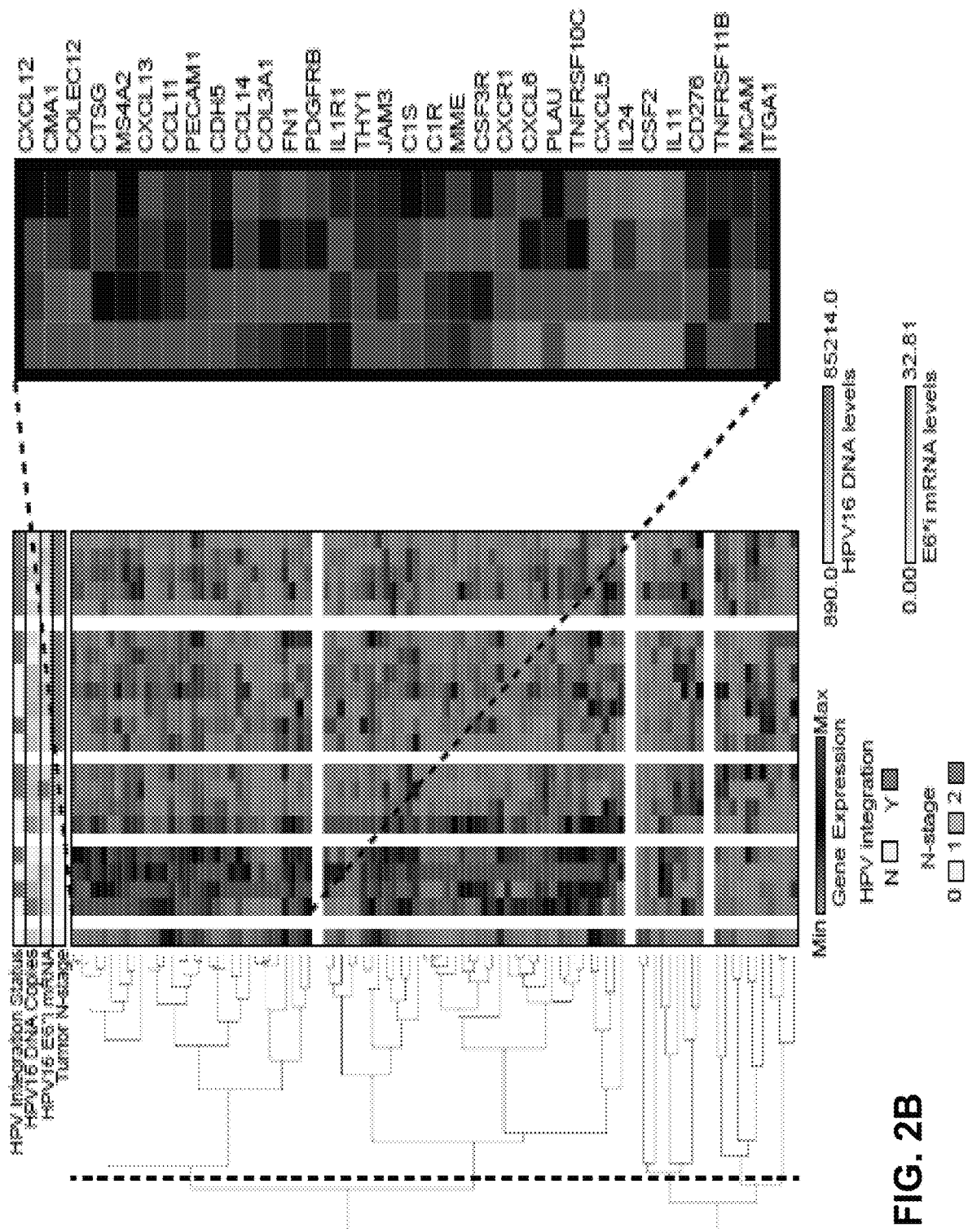

Next, unguided hierarchical clustering of tumor samples was performed based on genes that were differentially expressed either greater than 2-fold or reduced in expression by 50% (FIG. 2A). This method of analysis enabled visualization of several "hot-spots," or upregulated gene regions in four of six (66.7%) patients with N0 status. FIG. 2B displays the same data stratified by increasing node involvement (N=0, N=1, N=2) and further depicts these highly active gene expression regions in patients with no nodal involvement. Additionally, a global downregulation of most of the 770 genes analyzed was observed in patients with more advanced lymph node involvement (FIG. 2B).

Figure 3A:
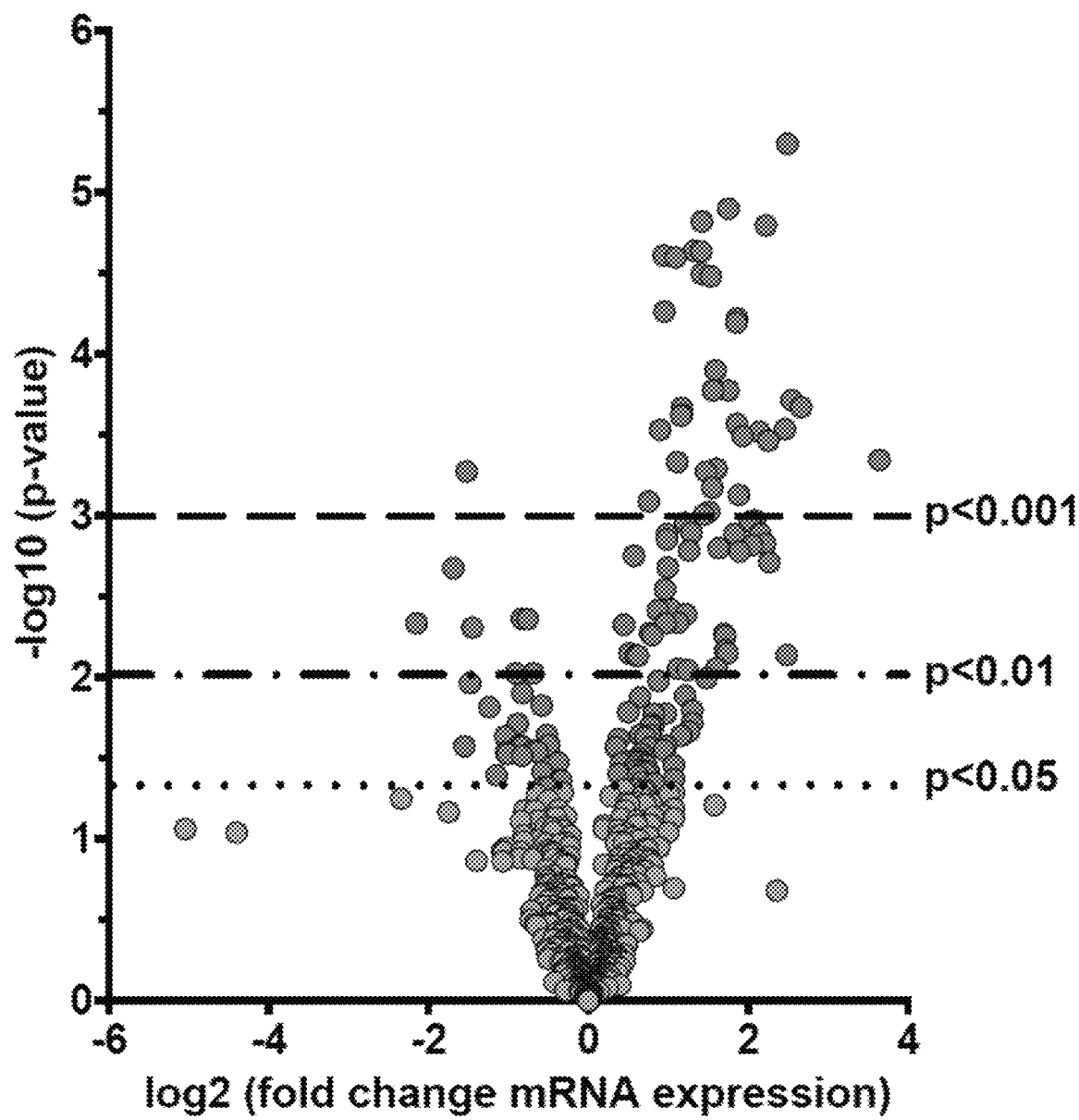
FIGS. 3A-3Q can demonstrate that an analysis of differentially expressed genes yields 15-gene molecular signature. Normalized, log 2 values of 164 differentially expressed genes (defined as log 2(N0 expression/N+ expression) were analyzed using nSolver Advanced Analysis Software.

Following the identification of gene hot spots in N0 tumors, nodal involvement based on a specific genetic signature was examined. Of the 650 genes that passed quality control metrics. 146 were significantly differentially expressed (FIG. 3A). Of these genes with significant differential expression, 63 were observed to be upregulated in LN negative disease compared to LN positive disease, and 11 genes were significantly downregulated.

Figure 3B:
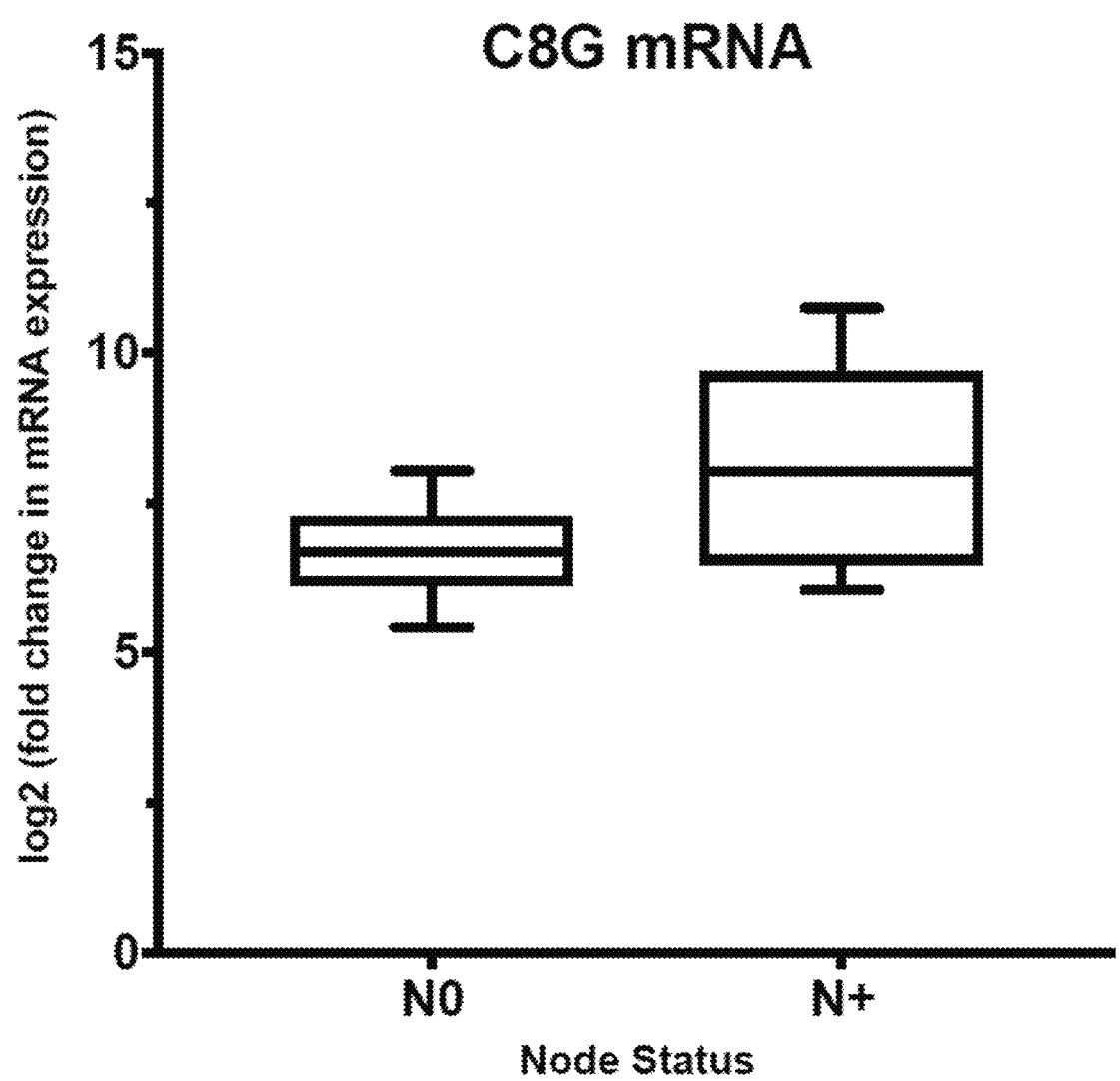
FIGS. 3B-3P. The top 15 most significant differentially expressed genes (10 upregulated and five downregulated) are plotted as Tukey box-and-whisker plots. Horizontal lines in each box represents the median value for the collective group of samples.
Figure 3C:
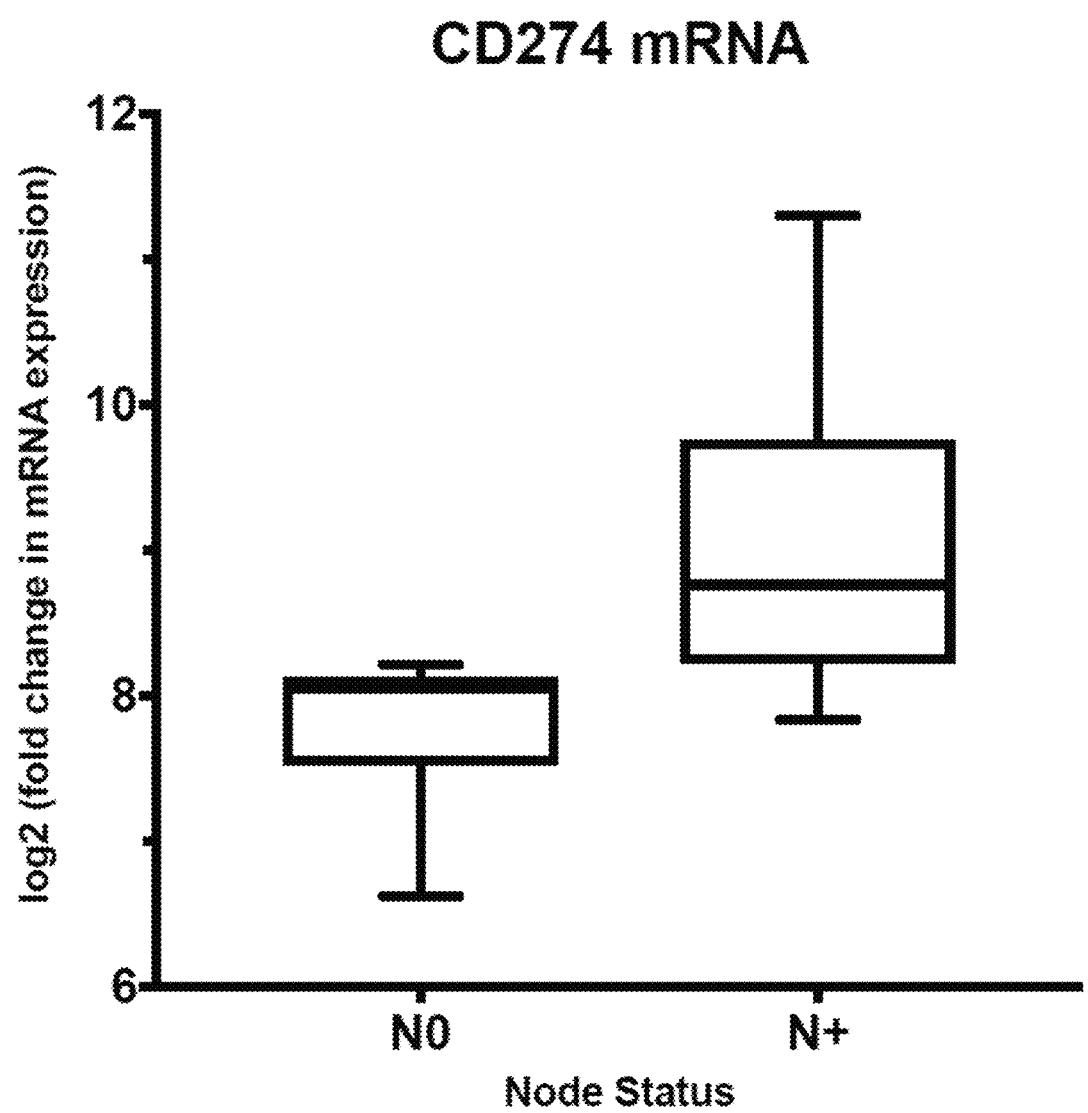
Figure 3D:
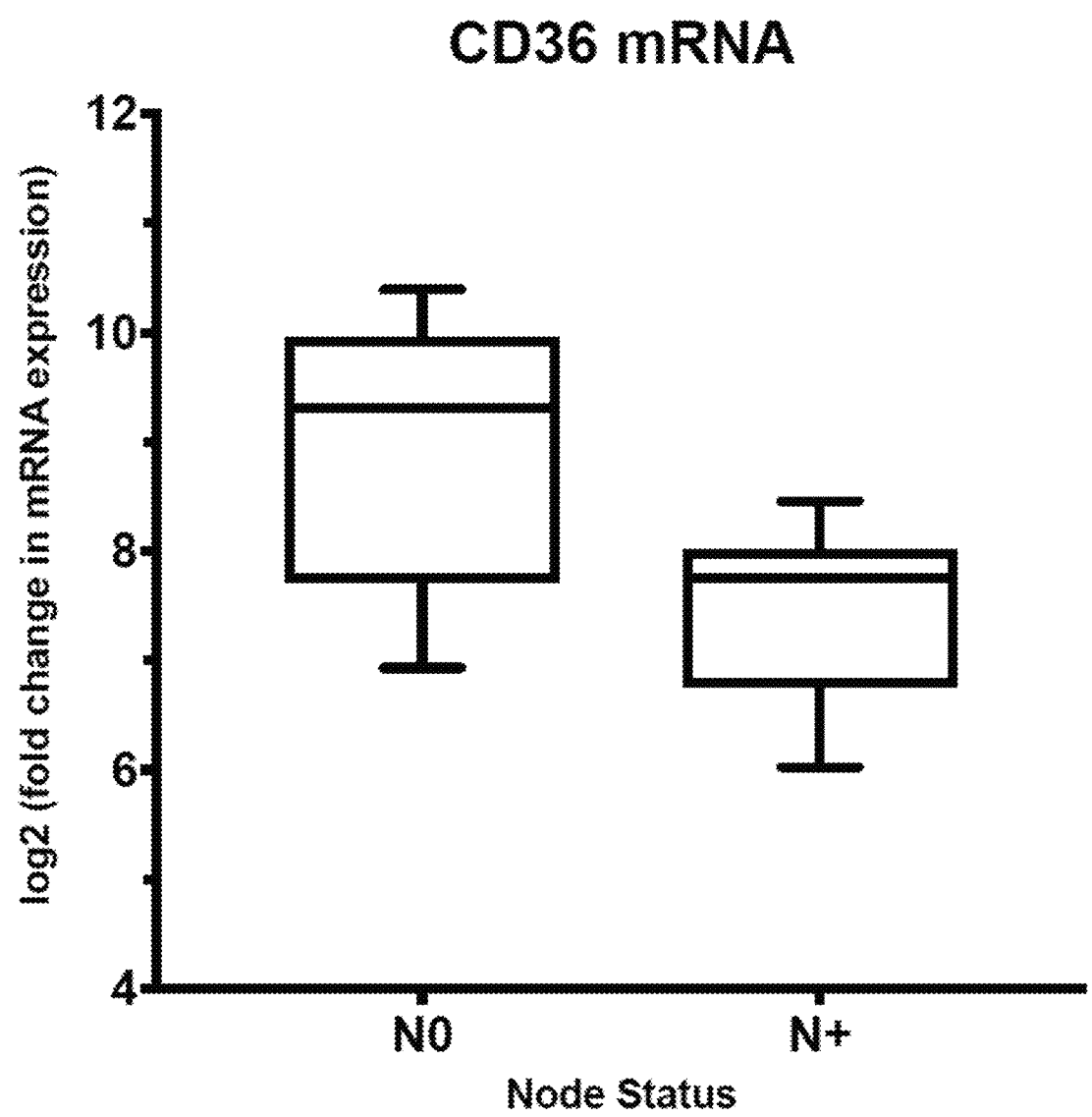
Figure 3E:
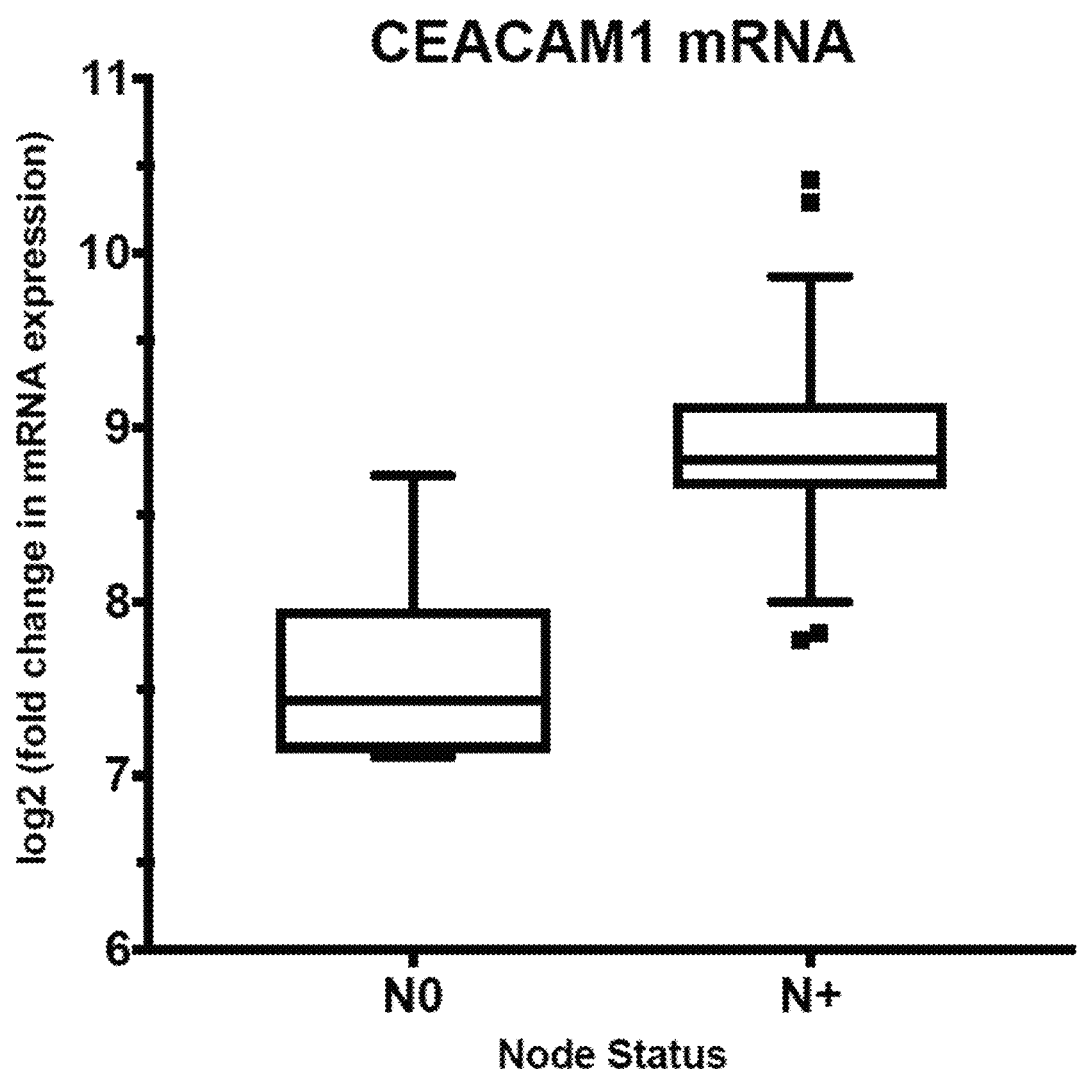
Figure 3F:
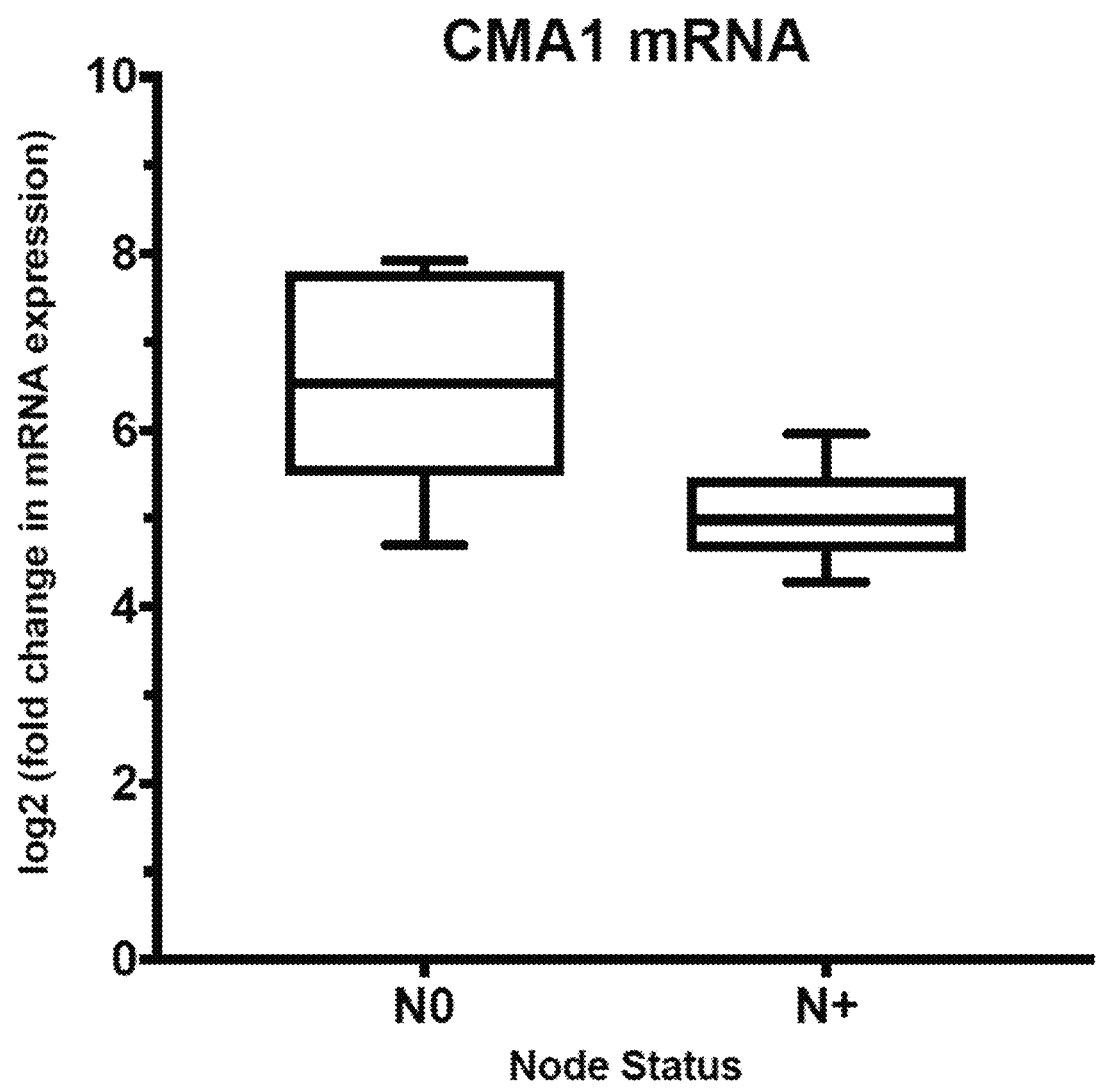
Figure 3G:
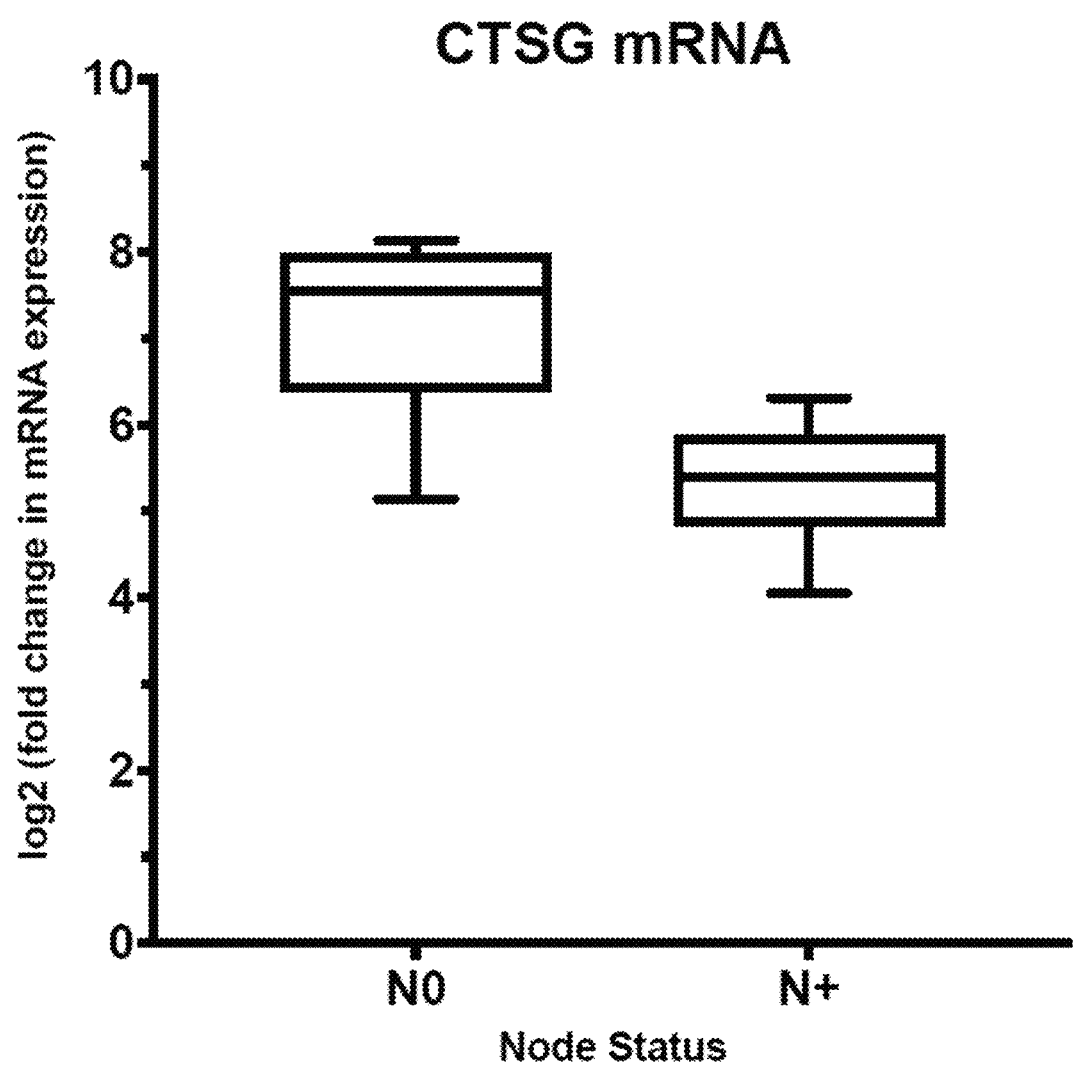
Figure 3H:
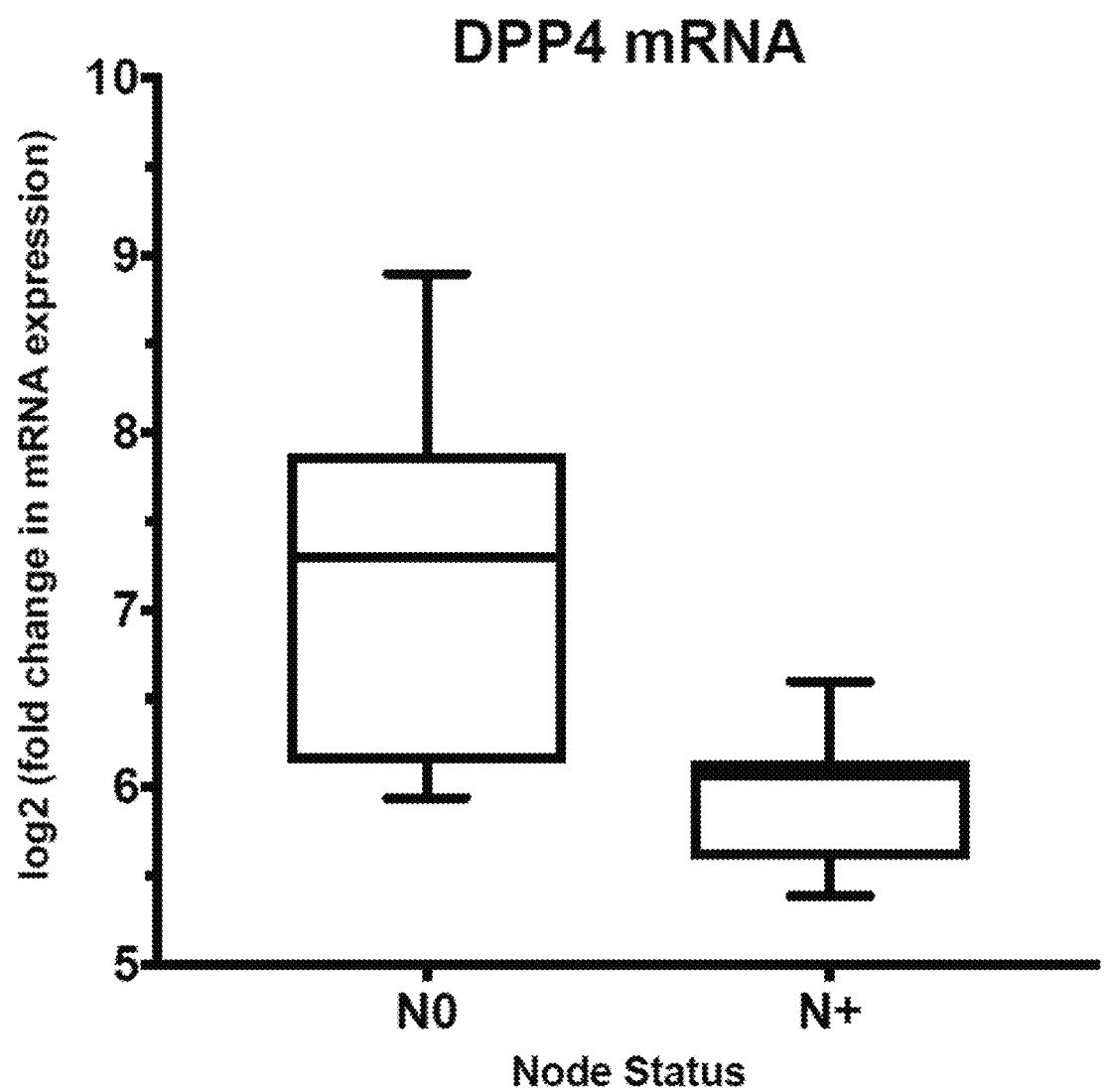
Figure 3I:
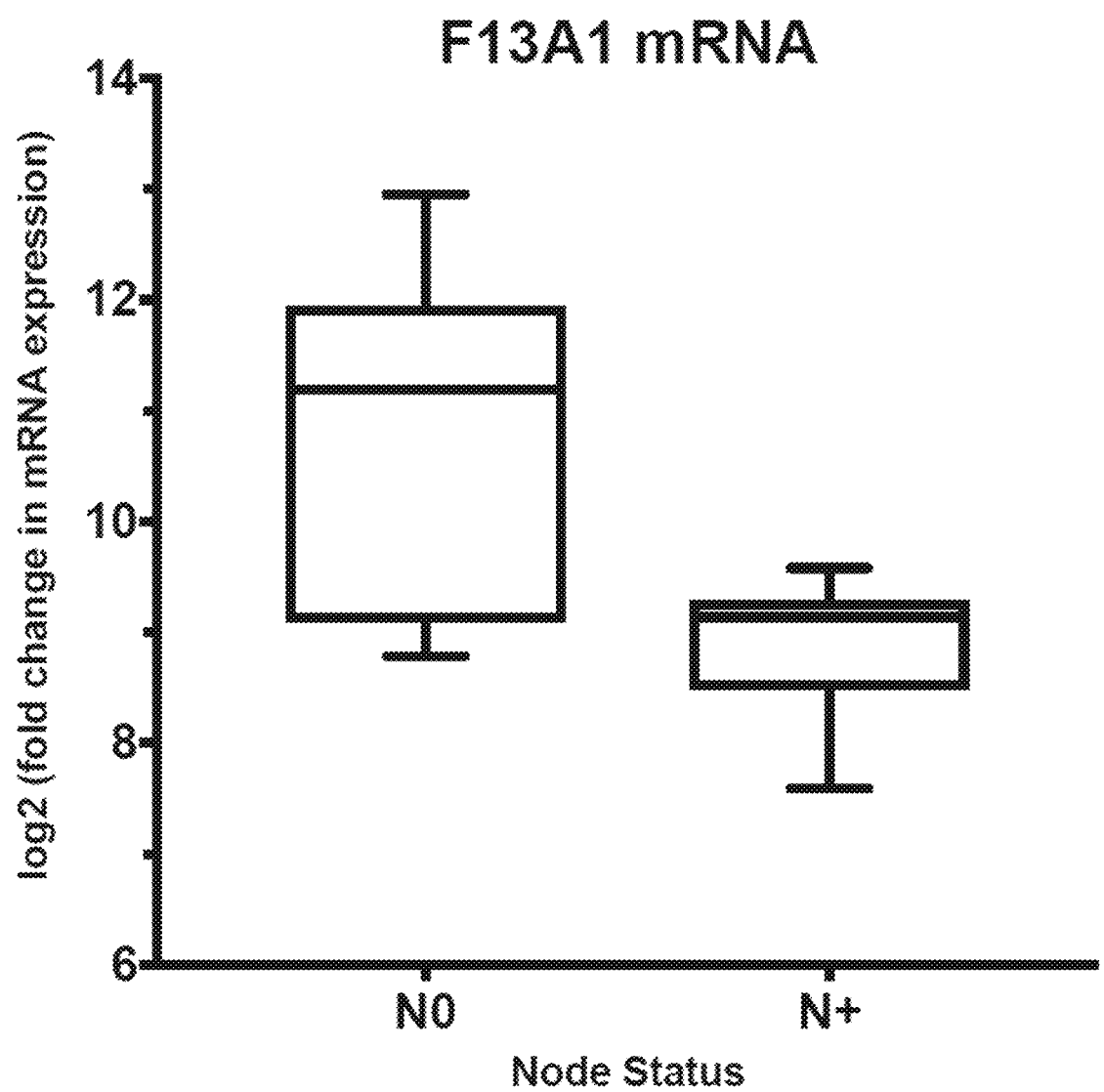
Figure 3J:
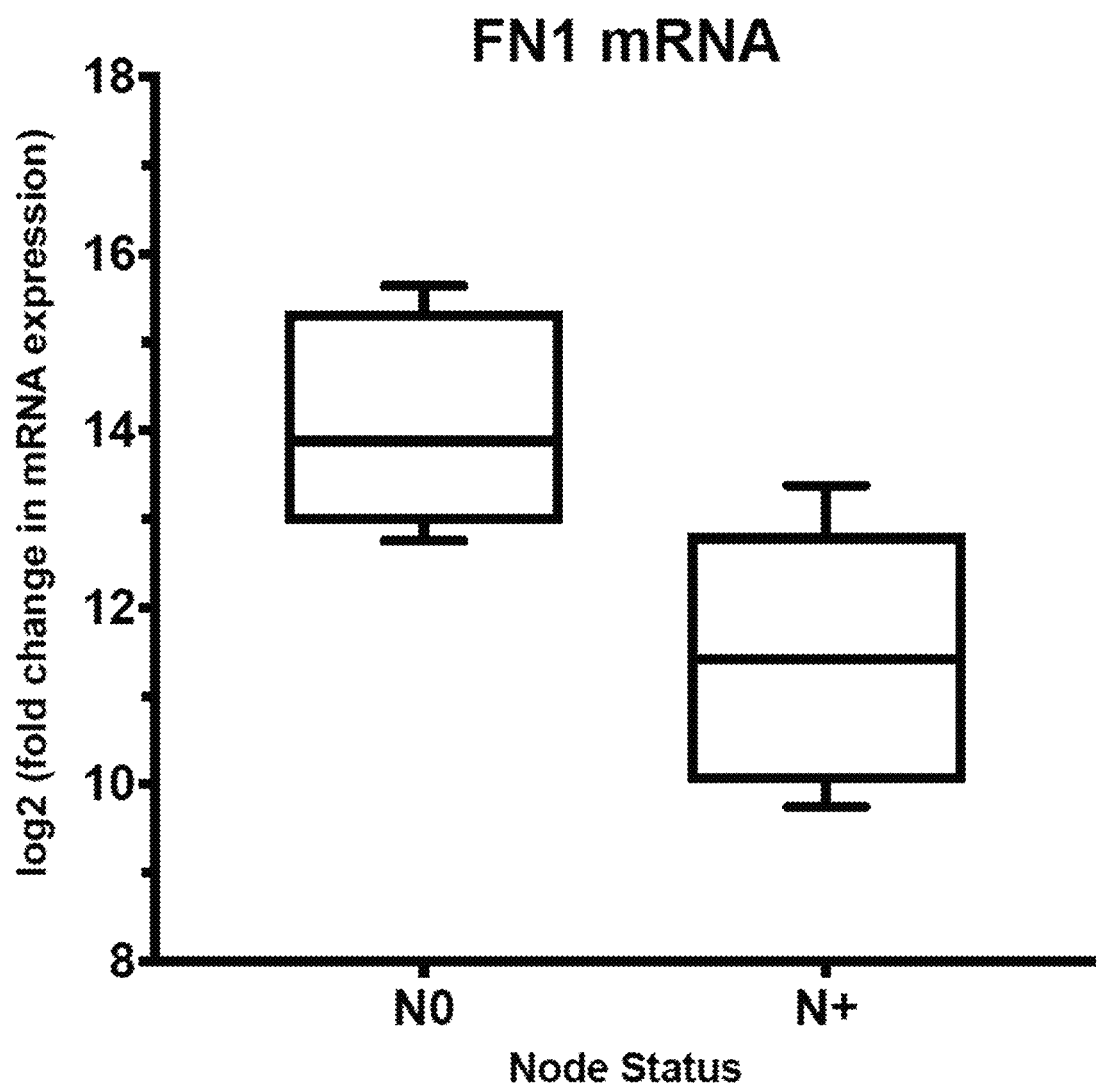
Figure 3K:
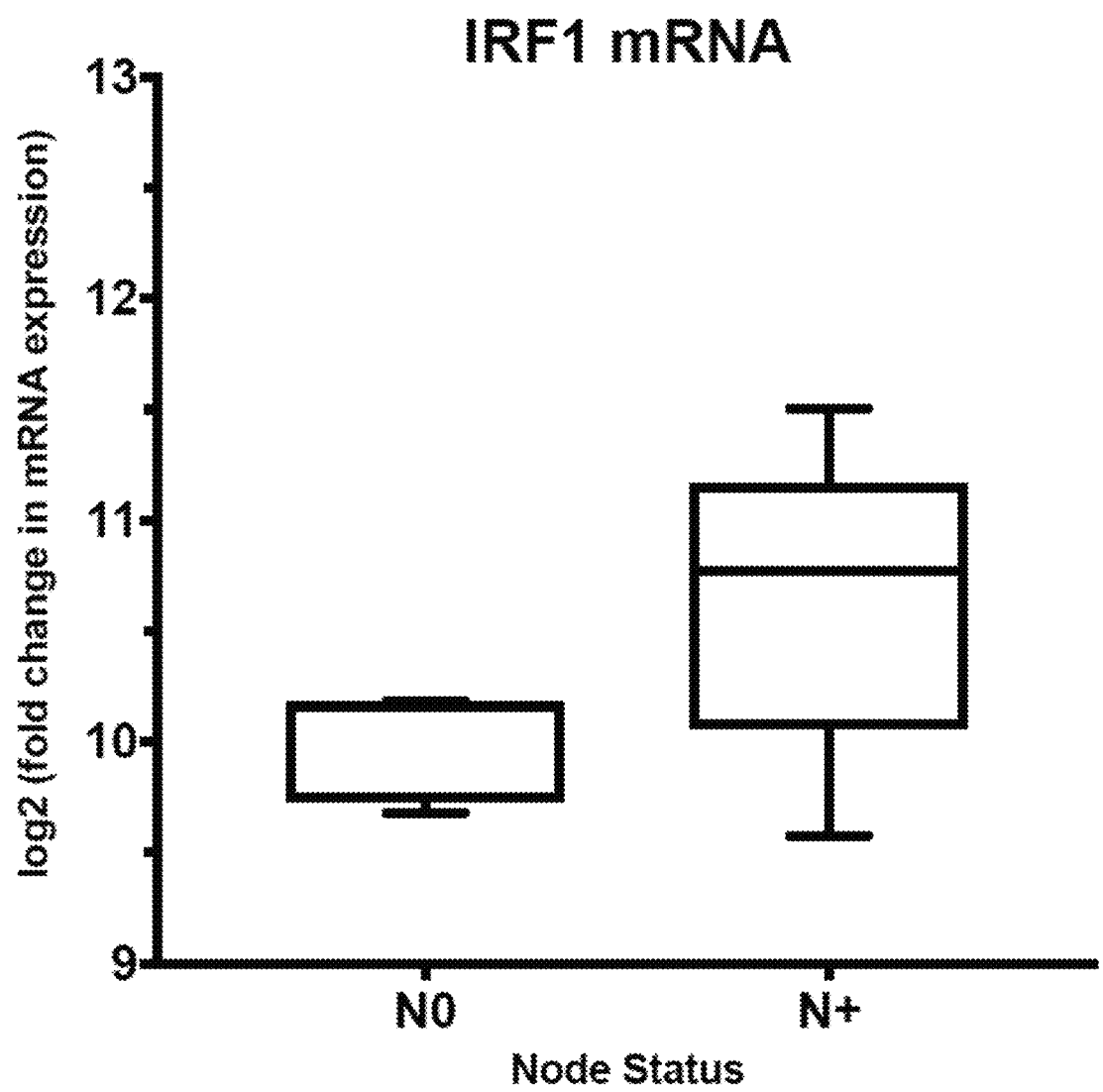
Figure 3L:
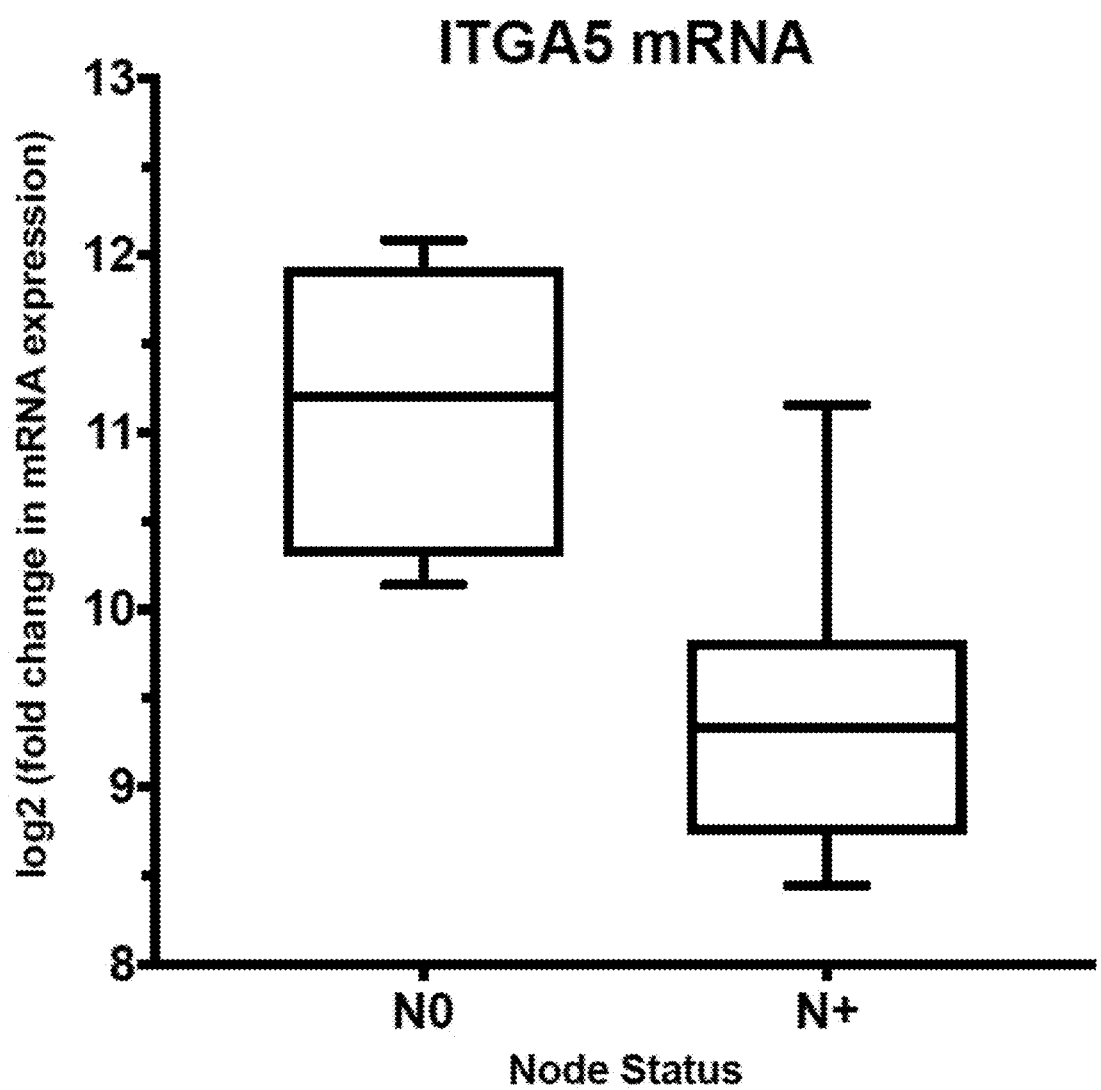
Figure 3M:
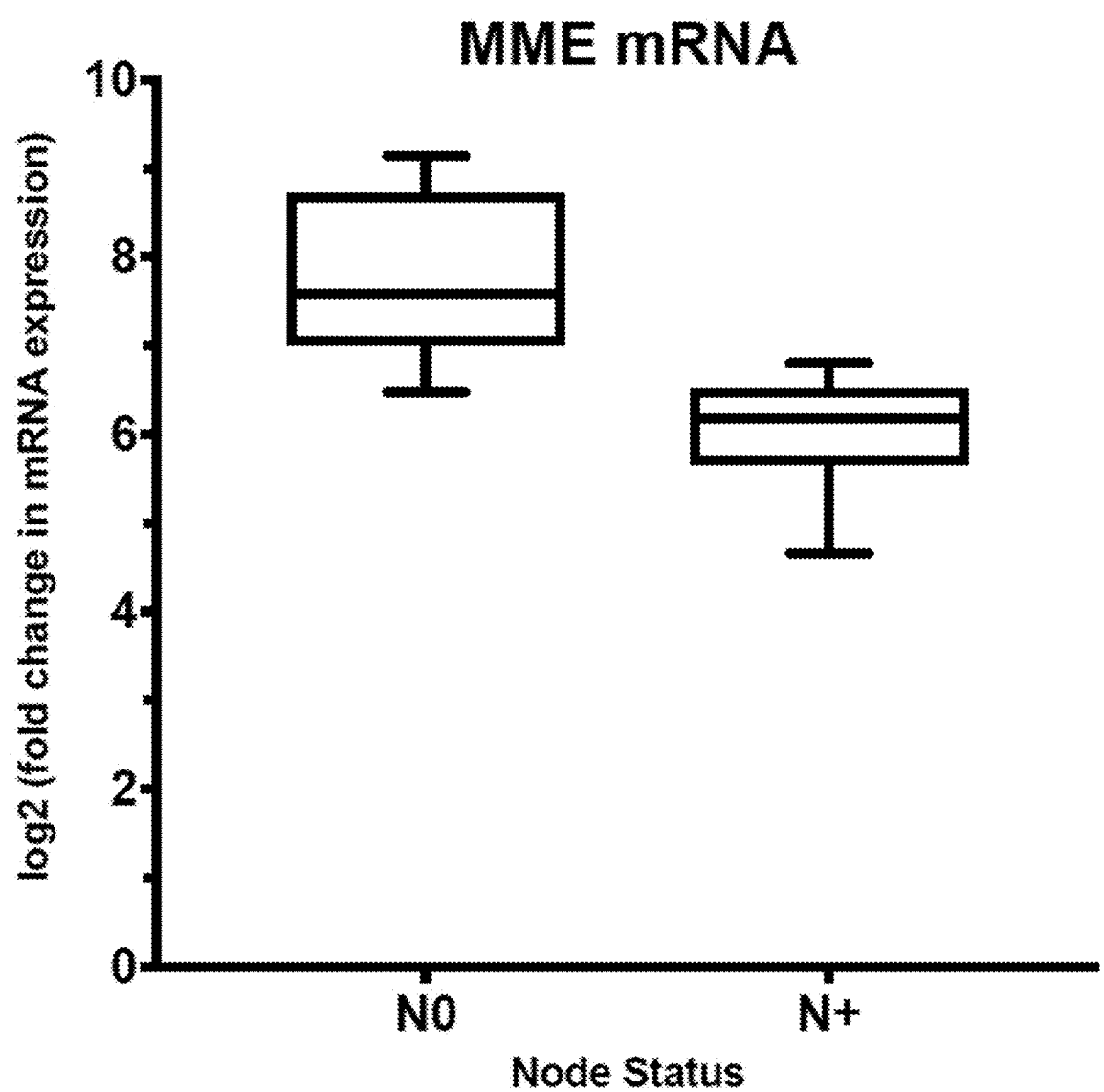
Figure 3N:
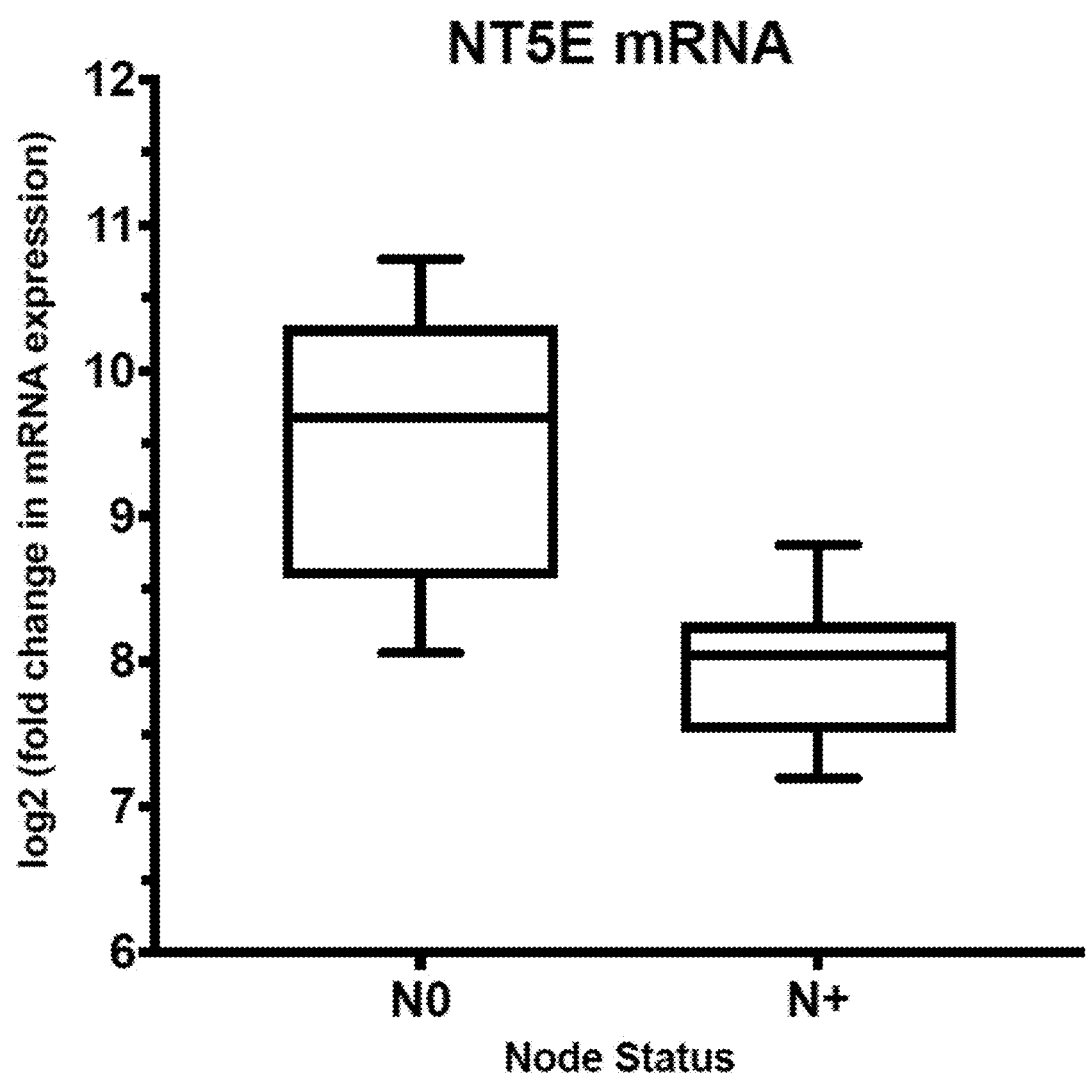
Figure 3O:
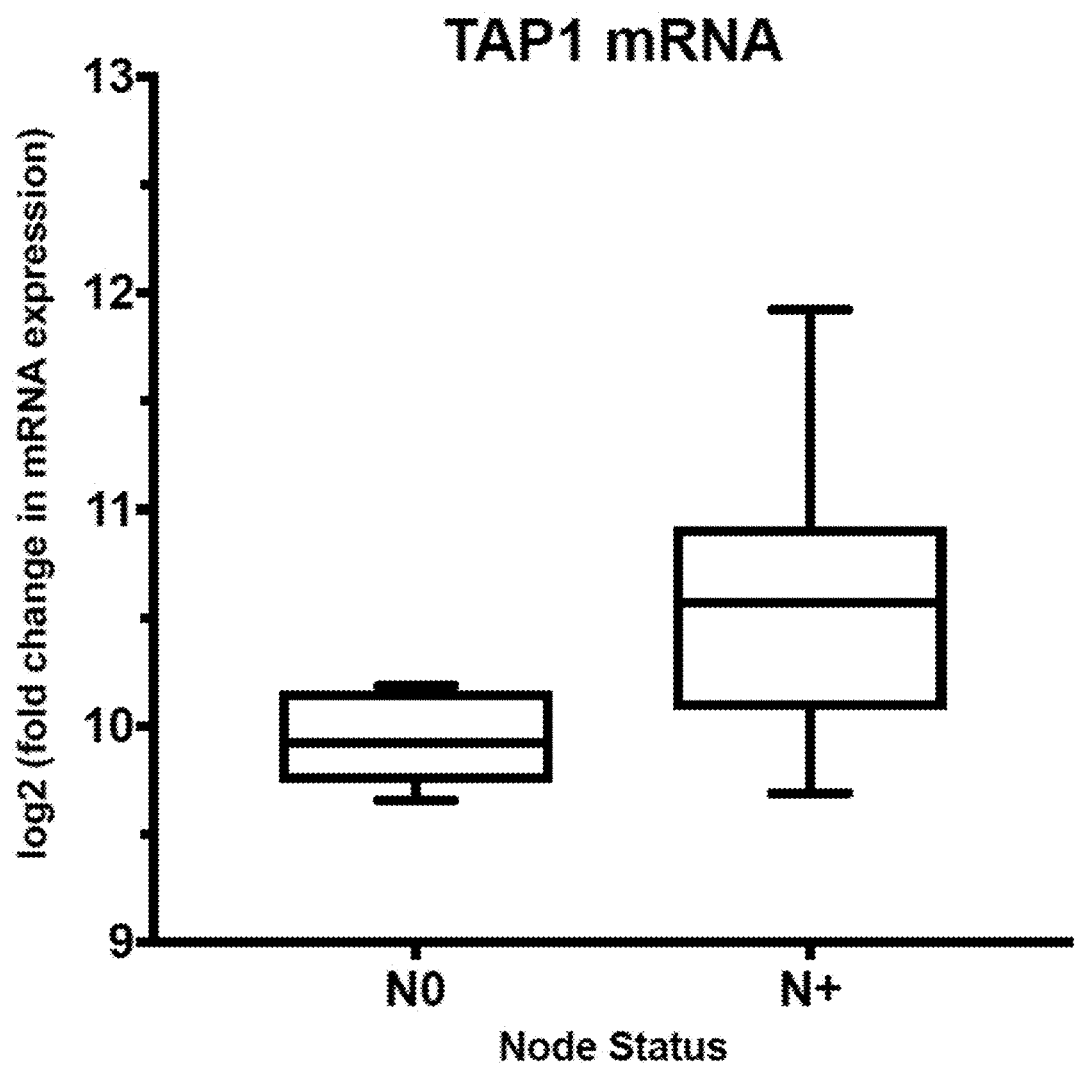
Figure 3P:
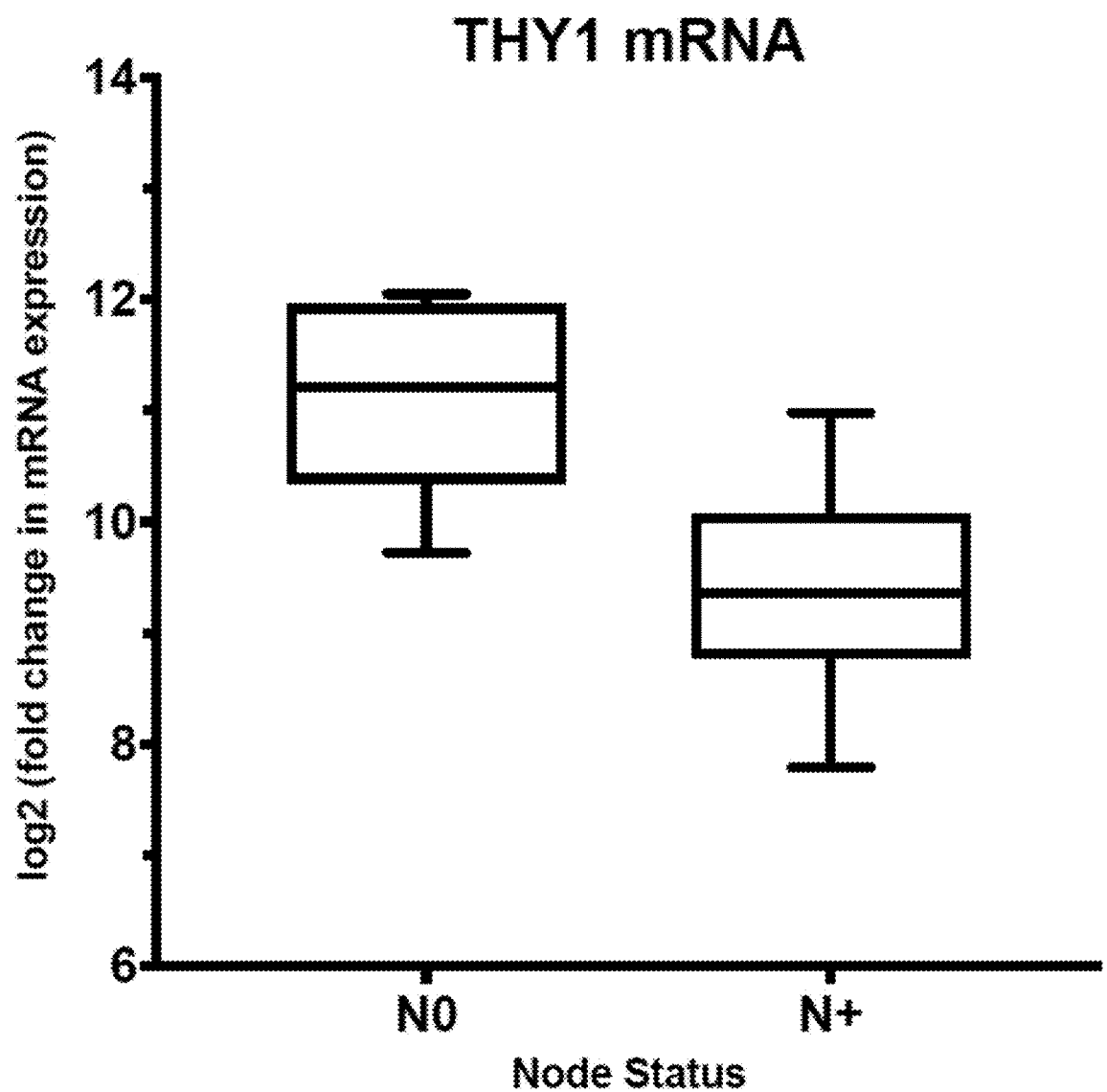
Figure 3Q:
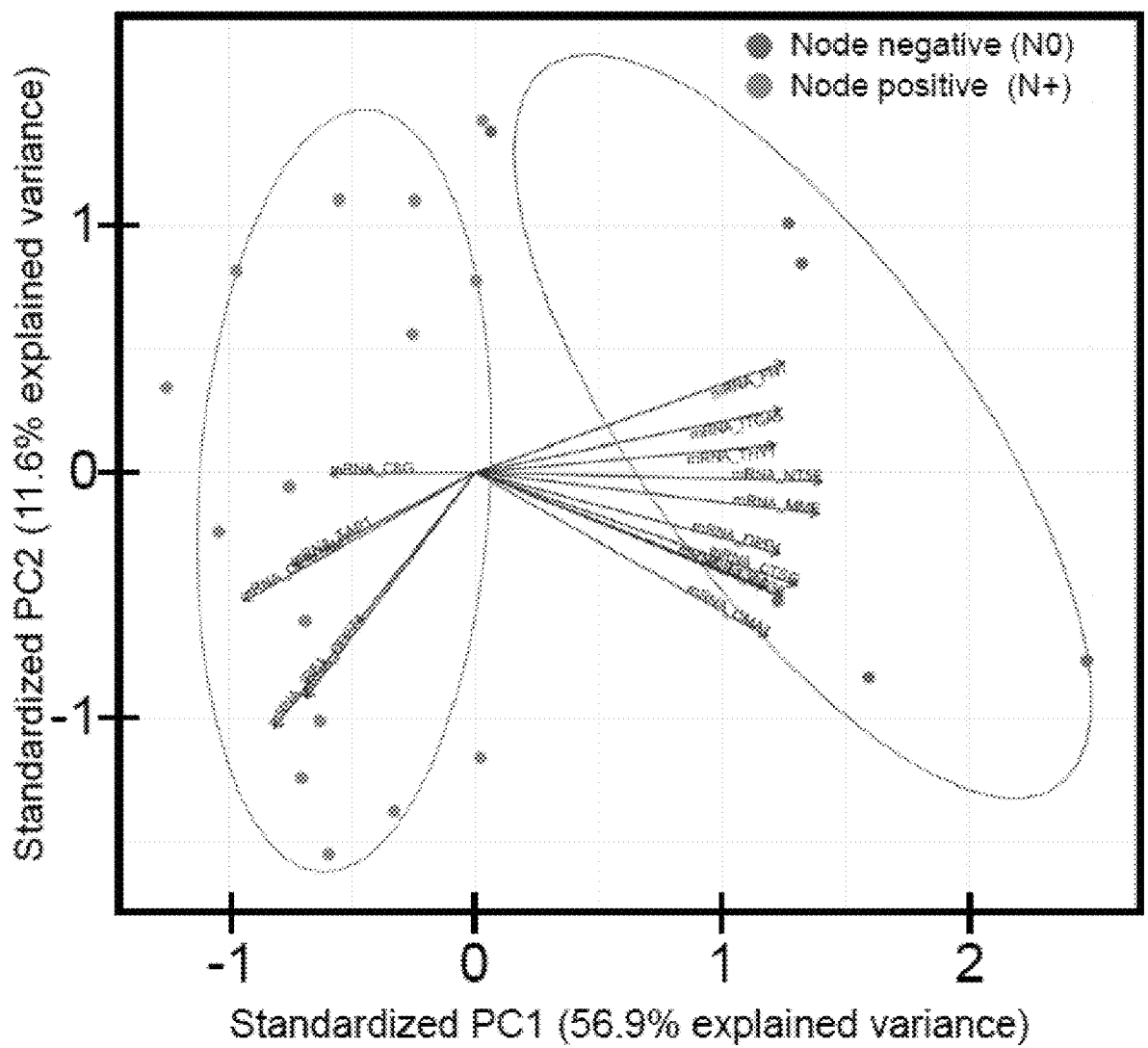

To develop a molecular signature for nodal involvement, the 10 most significantly upregulated and five most significantly downregulated genes were identified in tumor samples that were radiographically N0 (FIG. 3B). We then conducted a principal component analysis based on the gene expression values of these 15 differentially expressed genes which showed clear discrimination of LN negative versus LN positive OPSCC samples along the first two principal components and accounted for nearly 70% of the variance in gene expression (FIG. 3C).

The sensitivity and specificity of this test for detecting LN involvement was evaluated. Using these 15 genes, we found this profile had a sensitivity of 88% ($CI_{95}$ 63-98%) and specificity of 85.71% ($CI_{95}$ 42-99%). Given these test characteristics, the positive likelihood ratio was calculated to be 6.2 ($CI_{95}$ 1-38) and the negative likelihood ratio to be 0.14 ($CI_{95}$ 0.04-0.52). Further, it was determined that the population's prevalence of LN positive disease was 70.8%. Using these data, the positive- and negative-predicative values were calculated for this gene signature to be 94% ($CI_{95}$ 70-99%) and 75% ($CI_{95}$ 44-92%), respectively.

Figure 4A:
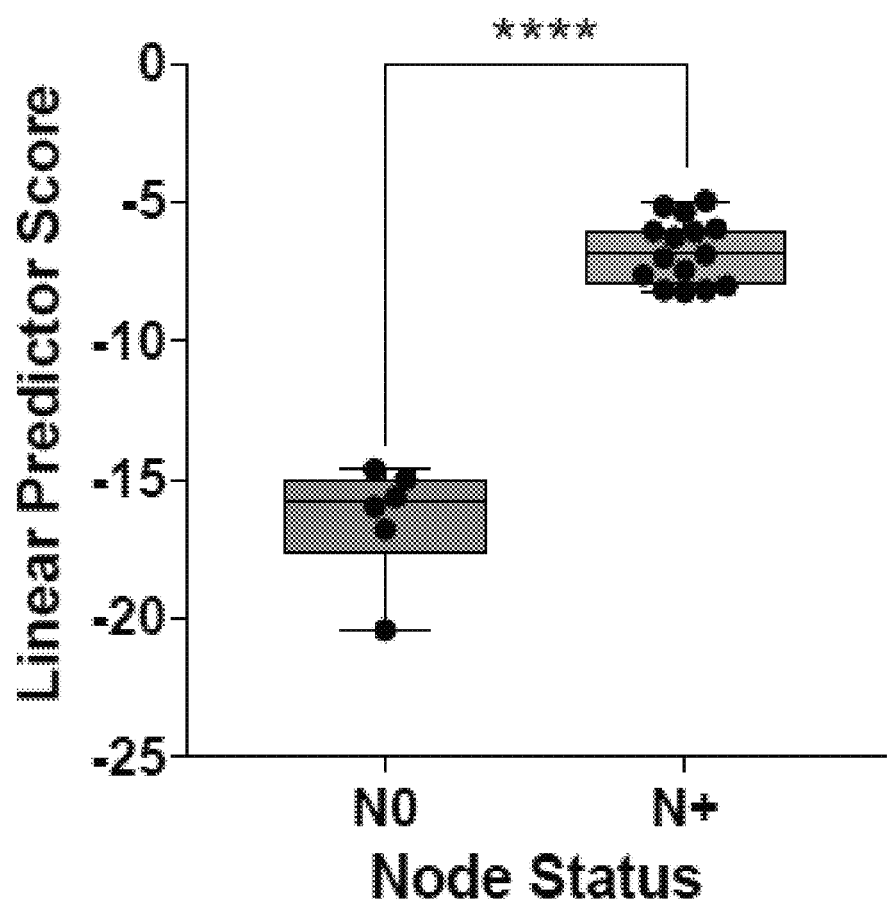
FIGS. 4A-4B can demonstrate that Machine learning yields a novel gene signature for N0 versus N+ HPV-driven OPSCC.

In addition to the selection of 10 upregulated and 5 downregulated genes, a machine learning module was used to compare our method to one that uses a gene signature training algorithm based on the elastic net, demonstrating a mean z-score difference between the two groups to be 9.6 ($CI_{95}$ 8.2-11.13) (FIG. 4A). Using this method, we developed a set of 40 genes that, when measured together, distinguished tumor samples that are biologically N0 from tumors that are N+ (area under the curve=0.933; 95% confidence interval, 0.633-1.00 by receiver operating characteristic curve analysis) (FIG. 4B), independent of clinical N-staging.

Discussion

Figure 4B:
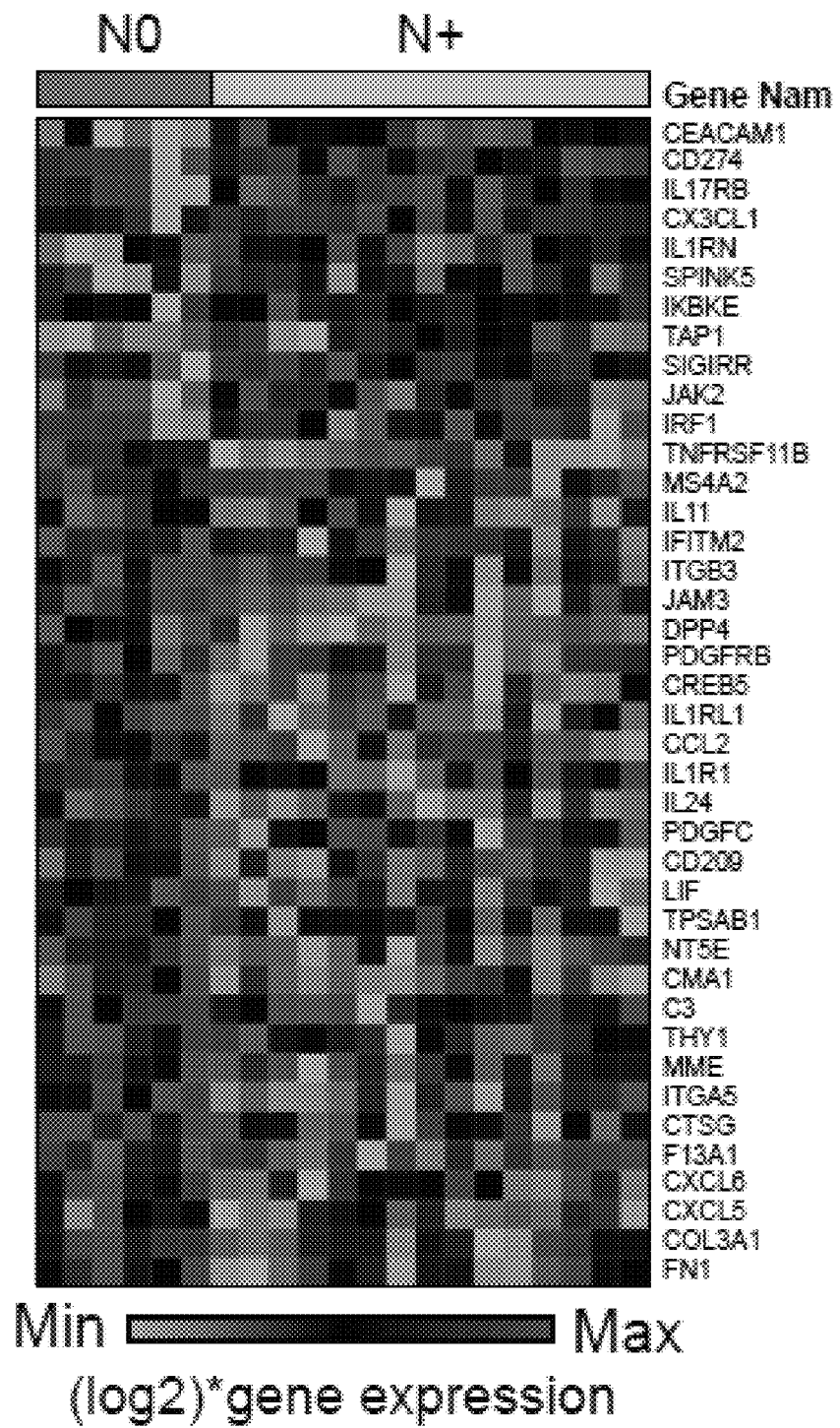
Figure 5:
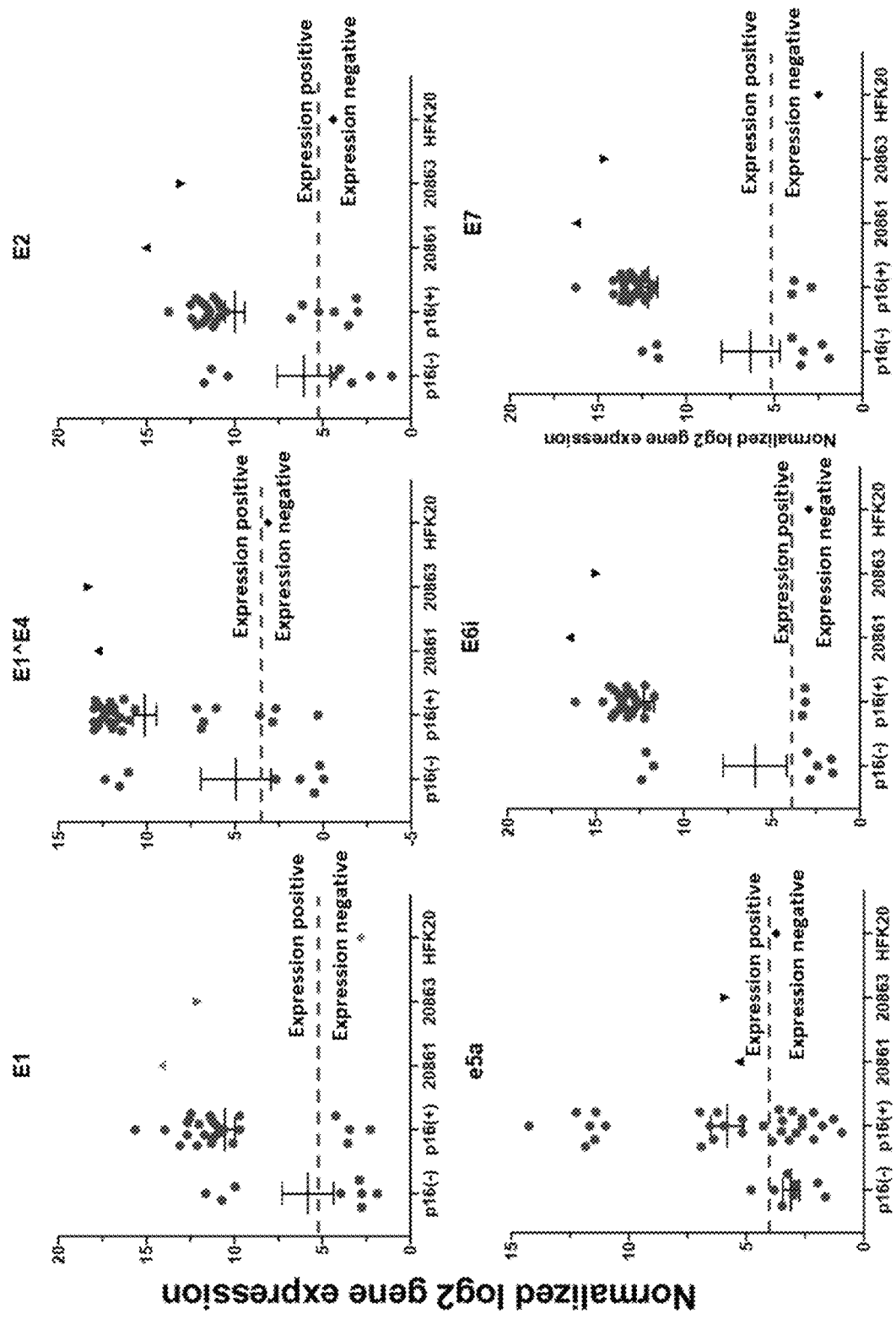
FIG. 5 shows HPV detection by RNA assay is more sensitive than p16 immunohistochemistry. p16(−), Clinically treated as HPV negative; p16(+), Clinically treated as HPV positive: 20861, integrated HPV16 cervical cancer cell line; 20863, Episomal HPV16 cervical cancer cell line; HFK20, normal human foreskin keratinocytes (HPV negative).
Figure 6A:
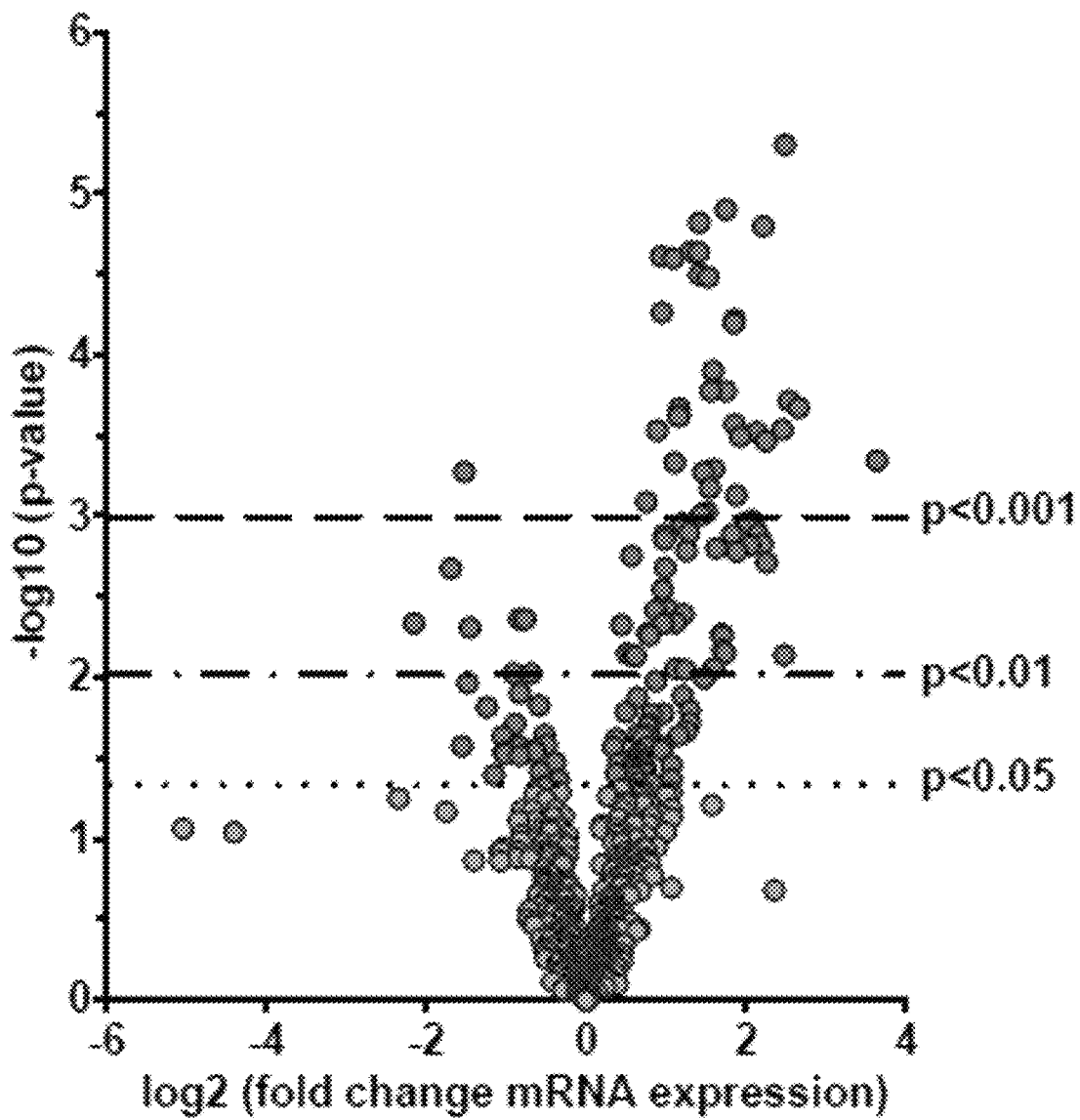
FIGS. 6A and 6B show Nanostring assay can give both HPV status and a "tumor aggression" profile.
Figure 6B:
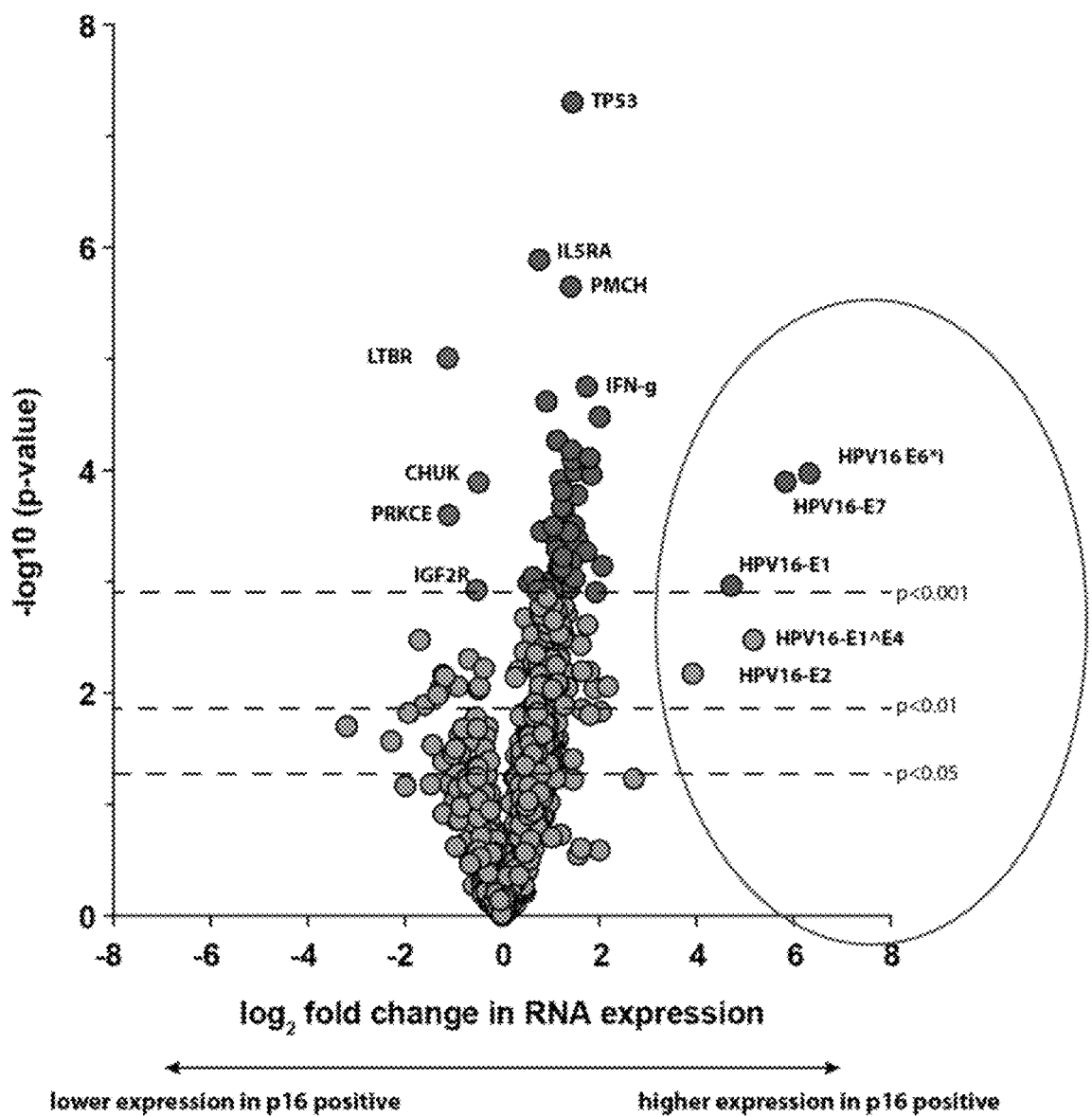

This Example examines and can demonstrate the onco-immune gene expression profile of HPV-positive OPSCC and determine potential differences in gene expression by nodal metastasis. The expression of several genes was correlated highly with clinical nodal status, as demonstrated by the distinct clustering pattern for N0 and N+ patients (FIGS. 1A and 2B); determined a set of differentially expressed genes between the two N-stages (FIG. 3A); and identified a gene expression signature associated with node positive versus node negative tumors (FIG. 4B). This gene signature can resolve different tumor phenotypes within the family of p16-positive OPSCCs.

Despite the widespread use of and recommendation for p16-IHC as surrogate for HPV-positive OPSCC (Lewis J S, et al. Arch Pathol Lab Med. 2017), there is currently no established molecular test to further stratify treatment or prognosis among known HPV-positive cases. This has led to multiple efforts to develop more refined prognostic biomarkers for OPSCC, including the use of HPV antibodies (Zhang Y, et al. Oral Oncol. 2017 67:77-82), IHC for multiple immune and tumor cell markers (DEK, PD-1, PD-1, PD-L2, EGFR, HER2, and HER3) (Steuer C E, et al. Mol Cancer Ther. 2018), and radiographic images as surrogates for molecular phenotypes (Rth L, et al. Br J Radiol. 2018: 20170498). Work by Keck et al. recently suggested a novel gene expression paradigm for HPV-positive OPSCC in which tumors are classified as either classical or inflammatory/mesenchymal (Keck M K, et al. Clin Cancer Res. 2015

21(4):870-881). The classical subtype includes expression of detoxification genes and may be associated with tobacco exposure, while the HPV inflammatory/mesenchymal subtype is associated with immune gene expression and shares characteristics with the atypical subtype characterized previously (Cancer Genome Atlas. Nature. 2015 517(7536): 576-582). Keck et al. demonstrated a trend towards improved survival in the HPV inflammatory/mesenchymal group compared to the HPV classical group (Keck M K, et al. Clin Cancer Res. 2015 21(4):870-881).

This Example addresses the limitations and failures of previous work by demonstrating a novel immune profile associated with nodal metastasis. The data herein can suggest that the sensitivity, specificity and positive- and negative predictive values using a tumor-based, molecular approach may supersede current testing methods that rely on p16-IHC alone (FIG. 3C). This can assist with treatment selection, as several clinical trials are currently evaluating the efficacy of treatment de-intensification for HPV-driven OPSCC (Chera B S, et al. Int J Radiat Oncol Biol Phys. 2015 93(5):976-985; Marur S, et al. J Clin Oncol. 2017 35(5): 490-497). The method and assay outlined herein could be used to stratify therapy or prognosis, similarly to the commercially available PAM50-based ProSigna™ assay developed for breast cancer recurrence risk (Parker J S, et al. J Clin Oncol. 2009 27(8):1160-1167; Wallden B, et al. BMC Med Genomics. 2015 8:54).

Given that a clear gene signature is present despite a small sample size demonstrates the potential power of this method to inform us about a tumor's biology. Further, this Example can demonstrate that p16-positive tumors are not necessarily biologically uniform and can demonstrate that a more refined approach to therapy is warranted. The data in this Example can demonstrate a more refined molecular analysis of tumors and benefits that can be obtained using it for treatment stratification. Given that not all p16-positive tumors have excellent outcomes, it is prudent to stratify therapy and recommend clinical trial de-intensification based on tumor biology as can be demonstrated by this Example.

Example 2

Using an expanded patient cohort, an assay for not only stratifying p16+N0 vs N+ disease, but also have modified the assay to natively detect the presence of high-risk HPV RNA was also developed via modeling, This can be an additional prognostic indicator for OPSCC. Within HPV+ subgroups, which patient tumors have integrated versus episomal viral genomes can be delineated. This is important, as patients with integration have a much stronger oncogenic drive, as HPV integrates in the E2 region of the viral genome. This results in uncontrolled expression of the oncoproteins, E6 and E7, which results in a higher degree of malignant transformation and a more aggressive disease.

Knowing whether or not a patient is a) HPV-positive and b) if they are HPV-positive, whether the viral genome is episomal or integrated changes the treatment strategy and subsequent treatment regimen of the subject as compared to the current "standard of care". In short, clinical decision making and treatment options can be expanding or limited the scope of therapies that are considered the "standard of care" for a specific patient based on determining if the patient is HPV positive and if they viral genome is episomal or integrated.

HPV-negative patients can receive maximum therapy, including surgical resection, chemotherapy, and radiotherapy at the highest doses. HPV-positive patients can be eligible for a less aggressive approach that can include primary radiotherapy alone (e.g. reduced side effect profiles from treatment), and certain patient cohorts with minimally invasive or aggressive disease may be eligible for further reduced-dose radiotherapy (e.g. even less side effects from treatment). However, patients with integrated HPV disease, do not benefit from reduced radiotherapy treatment and their disease course tracks more like that of an HPV-negative patient. As such, even if the patient is HPV positive they may need and can be eligible for a more aggressive therapy approach similar or the same as that applied to a HPV-negative patient.

The assay described in this Example can delineate the aggressiveness of the tumor using an RNA profile (e.g. identifying patterns more likely to be metastatic), delineate HPV positive from HPV negative disease using HPV specific markers, delineate p16-negative from p16-positive disease using specific gene expression profiles, and/or delineate integrated from episomal HPV-mediated disease.

The assay described in this Example can identify whether a patient has p16-related from p16-non-related disease. These are staged, treated, and managed in an entirely different manner from one another per AJCC 8 guidelines, which is followed by all practicing medical and surgical oncologists. The assay described in this Example can identify the presence of HPV-mediated disease. Tumors that are HPV-mediated are generally p16+(see above re: importance), but there are certain tumors that are HPV+ and p16− (or vice versa), and these tumors are often managed with respect to their p16 status, not HPV status. This assay improves the sensitivity and specificity for determining which treatment pathway a patient should be subjected to. The assay described in this Example can identify whether an HPV-mediated tumor is being driven by an integrated or episomal form of HPV. As previously discussed integrated HPV tumors should be treated in a manner more consistent with HPV-negative disease, as these tumors are oft refractory to standard HPV-positive treatments. This assay can aid in identifying these patients a move them to the "other" treatment track.

Example 3

The goal of this Example was to identify a statistical approach and gene set which would reliably identify HPV+ oropharyngeal SCC patients with or without nodal metastasis; in such a way that was robust to cross validation.

Methods

Figure 7:
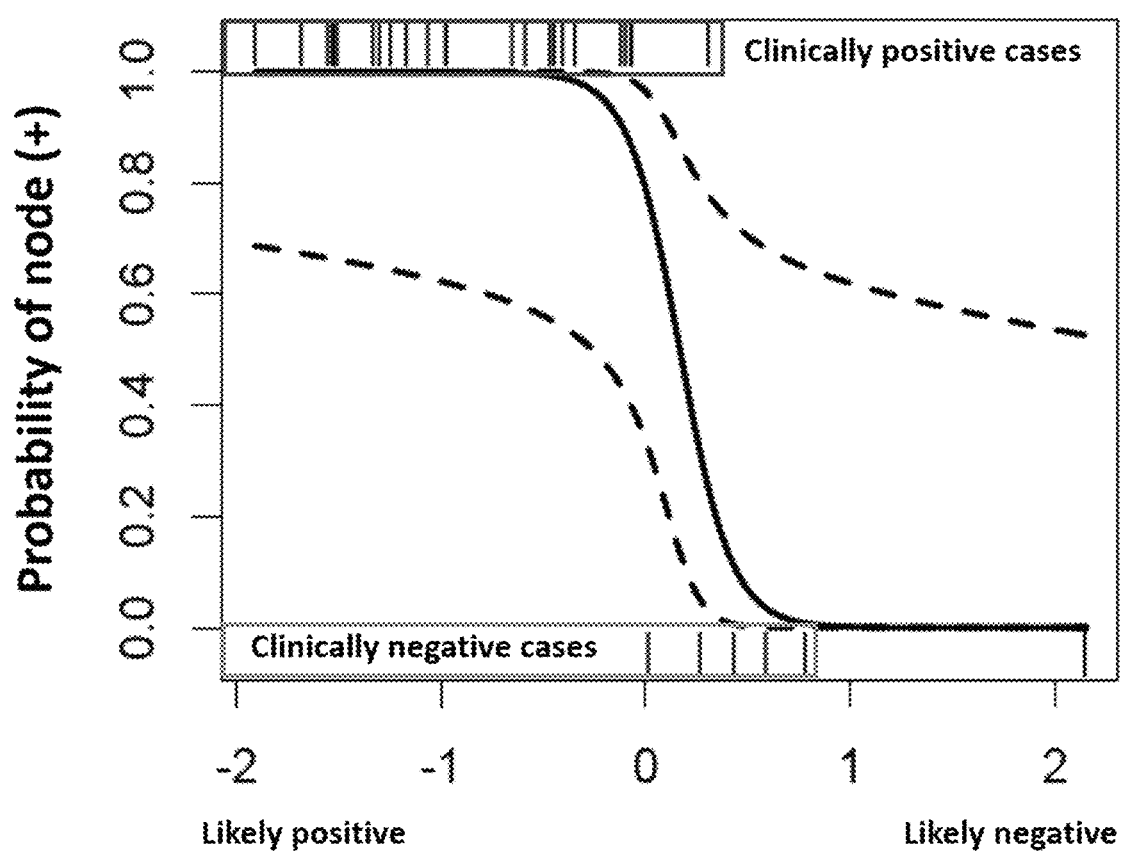
FIG. 7 shows modeling using "leave one out" statistical testing based on top 20 most DE genes.
Figure 8A:
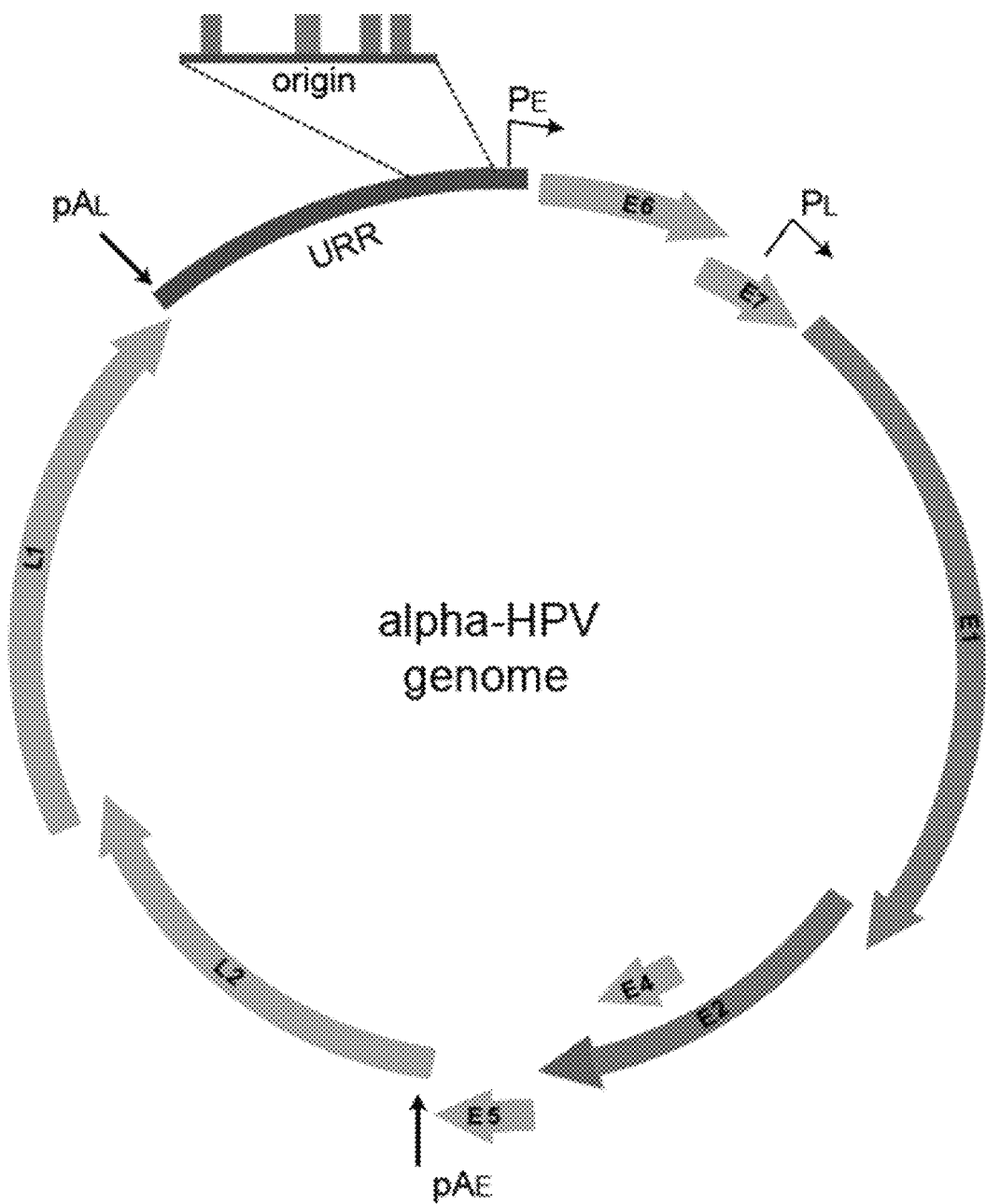
FIGS. 8A and 8B illustrate the use of the ratio of E6 to E5 as a predictor of HPV integration. Episomes have low E6:E5 ratio due to mono-cistronic expression and E2 control of E6/E7 levels. Integrated genomes have lost the ability for E2 to control E6 levels, so there is a higher E6.E5 ratio (FIG. 8B).
Figure 8B:
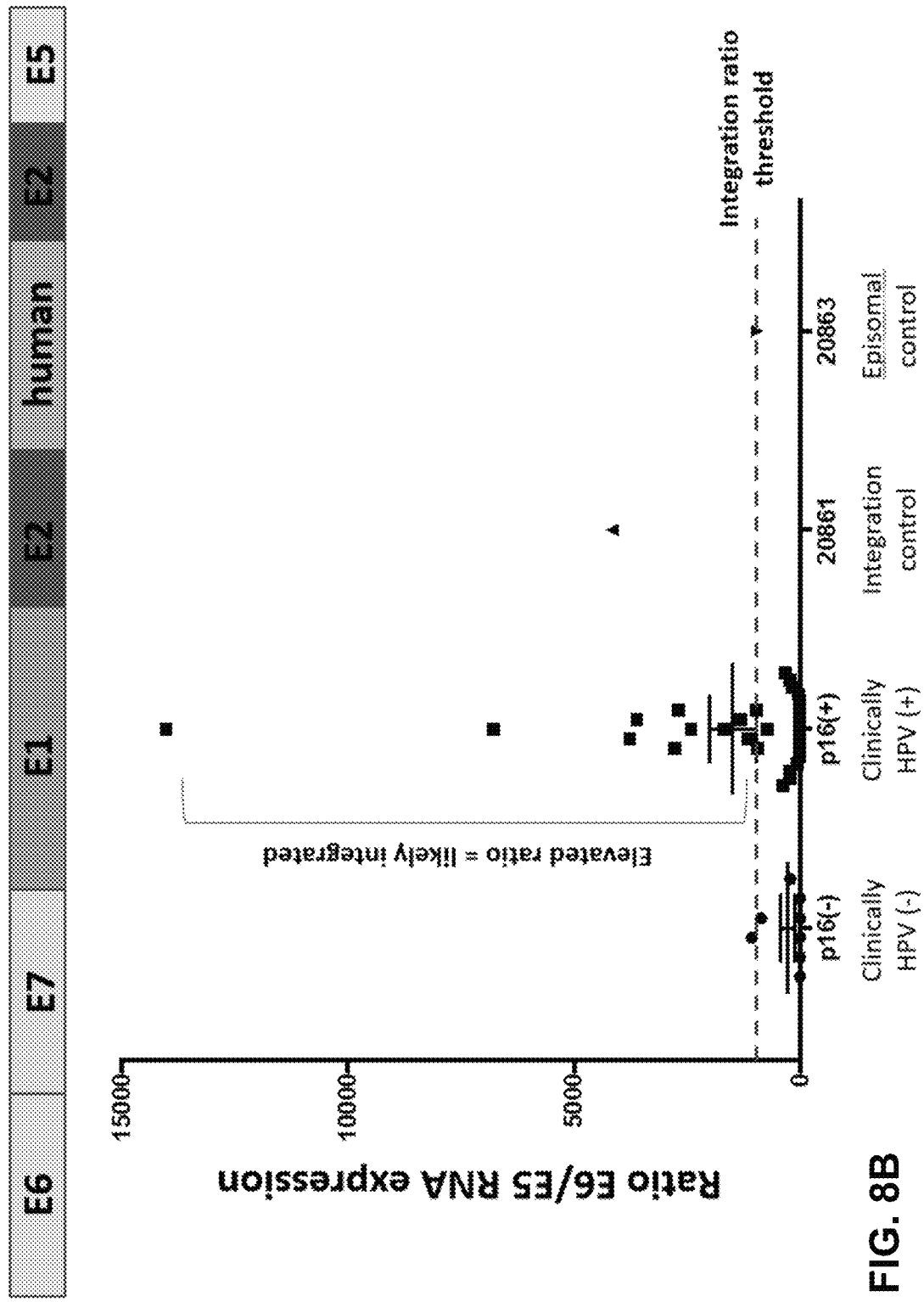

Starting with Log 2 normalized expression levels and clinical data differential expression analysis was performed using a generalized linear model-based approach; comparing node negative and node positive tumors. From this analysis genes were ranked by p-values. Multiple nearest centroid based predictors, using standard methods, were developed using increasing numbers of genes from the data, starting with the most differentially expressed gene. Performance was assayed by examining correct classification of both node negative and positive tumors. Optimal performance was identified using the 20 most differentially expressed genes (by p-value). Validation of the developed 20 gene, nearest centroid based predictor was performed using a leave one out cross-validation approach. Predictions and metrics included herein represent the cross-validation (FIG. 7). Perfect predictor performance (no miss-classifications) was seen when all available data was used for both training and prediction.

Results

A set of 20 genes was identified that can reliably identify node negative or positive HPV+ oropharyngeal SCC patients based on the tumor Nano-string data (Table 12). This gene set in combination with a nearest centroid based predictor is both highly sensitive and specific for nodal status based on ross-validation (Table 11).

TABLE 11

| Test Characterization | | | |
|---|---|---|---|
| Statistic | Formula | Value | 95% CI |
| Sensitivity | $\frac{a}{a+b}$ | 95.83% | 78.88% to 99.89% |
| Specificity | $\frac{d}{c+d}$ | 100% | 54.07% to 100.00% |
| Positive Likelihood Ratio | $\frac{\text{Sensitivity}}{1-\text{Specificity}}$ | | |

TABLE 11-continued

| Test Characterization | | | |
|---|---|---|---|
| Statistic | Formula | Value | 95% CI |
| Negative Likelihood Ratio | $\frac{1-\text{Sensitivity}}{\text{Specificity}}$ | 0.04 | 0.01 to 0.28 |
| Disease Prevalence | $\frac{a+b}{a+b+c+d}$ | 80.00% (*) | 61.43% to 92.29% |
| Positive Predictive Value | $\frac{a}{a+c}$ | 100.00% (*) | |
| Negative Predictive Value | $\frac{d}{b+d}$ | 85.71% (*) | 46.83% to 97.61% |
| Accuracy | $\frac{a+d}{a+b+c+d}$ | 96.67% (*) | 82.78% to 99.92% |

TABLE 12

20 genes involved in nodal mets predictor model using leave one out analysis

| ENTREZID | log2FC | AveExpr | t | P.Value | adj. P. Val | −log10pvalue |
|---|---|---|---|---|---|---|
| IRF1 | 0.11272457 | 10.7859205 | 4.12812593 | 0.0002483 | 0.02959876 | 3.60502113 |
| THBS1 | −0.1907647 | 10.8359856 | −4.1040414 | 0.00026573 | 0.02959876 | 3.57556208 |
| ITGB3 | −0.2168595 | 10.0385575 | −4.1886899 | 0.00020929 | 0.02959876 | 3.6792579 |
| MME | −0.322323 | 10.0872986 | −4.1043667 | 0.00026549 | 0.02959876 | 3.57595976 |
| IL1R1 | −0.1384892 | 10.5590404 | −3.9953803 | 0.00036047 | 0.02959876 | 3.44312846 |
| FN1 | −0.2507034 | 10.9674254 | −4.0086011 | 0.00034738 | 0.02959876 | 3.45919832 |
| MS4A2 | −0.2332307 | 10.0579942 | −4.0255145 | 0.0003313 | 0.02959876 | 3.4797746 |
| CMA1 | −0.3563313 | 9.8134876 | −4.0749277 | 0.0002884 | 0.02959876 | 3.54000133 |
| CTSG | −0.3532879 | 9.94749881 | −3.9972591 | 0.00035858 | 0.02959876 | 3.44541139 |
| PRKCD | 0.09464533 | 10.7080509 | 3.83039413 | 0.00057057 | 0.04147892 | 3.24369051 |
| FLT3LG | 0.11263743 | 10.6486909 | 3.80186452 | 0.00061741 | 0.04147892 | 3.20942429 |
| ENG | −0.0801307 | 10.7666898 | −3.6573281 | 0.00091848 | 0.05656313 | 3.03692978 |
| TAP2 | 0.10321826 | 10.8735398 | 3.62749607 | 0.00099639 | 0.05664098 | 3.00157033 |
| C3 | −0.1901936 | 10.7582555 | −3.5573726 | 0.00120558 | 0.06363742 | 2.91880381 |
| TAP1 | 0.12272375 | 10.7843198 | 3.48579885 | 0.00146267 | 0.07206076 | 2.83485434 |
| PDGFC | −0.2002982 | 10.4984247 | −3.3473702 | 0.0021178 | 0.08927855 | 2.67411577 |
| CD274 | 0.21047651 | 10.5210103 | 3.275862 | 0.0025587 | 0.08927855 | 2.59198025 |
| CX3CL1 | 0.16338627 | 10.7178888 | 3.28579335 | 0.00249259 | 0.08927855 | 2.60334929 |
| THY1 | −0.1615382 | 10.7107511 | −3.3185877 | 0.00228571 | 0.08927855 | 2.64097932 |
| IKBKE | 0.13139734 | 10.7744547 | 3.27599113 | 0.00255783 | 0.08927855 | 2.59212798 |

BOLD - also 1 of original 15 gene signature

We Claim:

1. A method of treating a tumor in a subject, the method comprising:
   a) detecting elevated p16 expression in the tumor;
   b) detecting elevated gene expression of C8G, CD274, CEACAM1, IRF1, and TAP1, and reduced gene expression of CD36, CMA1, CTSG, DPP4, F13A1, FN1, ITGA5, MME, NT5E, and THY1 and
   c) treating the subject with surgical resection, chemotherapy, and radiotherapy.

2. The method of claim 1, The method of claim 1, wherein step b) consists of:
   detecting elevated gene expression of CEACAM1, CD274, IL17RB, CX3CL1, IL1RN, SPINK5, IKBKE, TAP1, SIGIRR, JAK2, IRF1, and C8G; and detecting reduced gene expression of TNFRSF11B, MS4A2, IL11, IFITM2, ITGB3, JAM3, DPP4, PDGFRB, CREB5, IL1RL1, CCL2, IL1R1, IL24, PDGFC, CD209, LIF, TPSAB1, NT5E, CMA1, C3, THY1, MME, ITGA5, CTSG, F13A1, CXCL6, CXCL5, COL3A1, FN1, and CD36.

3. The method of claim 1, wherein step b) consists of detecting elevated gene expression of C8G, CD274, CEACAM1, IRF1, and TAP1; and step b) consists of detecting reduced gene expression of CD36, CMA1, CTSG, DPP4, F13A1, FN1, ITGA5, MME, NT5E, and THY1.

4. The method of claim 1, wherein step b) consists of detecting elevated gene expression of C8G, CD274, CEACAM1, IRF1, and TAP1; and step b) consists of detecting reduced gene expression of CD36.

5. The method of claim 1, wherein step b) consists of detecting reduced gene expression of CD36, CMA1, CTSG, DPP4, F13A1, FN1, ITGA5, MME, NT5E, and THY1.

6. The method of claim 1, further comprising determining if the subject is HPV positive.

7. The method of claim 6, further comprising determining in the HPV positive that the HPV is integrated.

8. The method of claim 7, comprising measuring the ratio of E6: E5 RNA expression, wherein an elevated E6: E5 ratio is an indication that the HPV is integrated.

* * * * *

SEQUENCE LISTING

<160> NUMBER OF SEQ ID NOS: 6

<210> SEQ ID NO 1
<211> LENGTH: 28
<212> TYPE: DNA
<213> ORGANISM: Artificial Sequence
<220> FEATURE:
<223> OTHER INFORMATION: Synthetic Construct

<400> SEQUENCE: 1
caagacagta ttggaactta cagaggtg                                      28

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

```
<400> SEQUENCE: 2
ctggcctcta tagtgcccag c                                              21

<210> SEQ ID NO 3
<211> LENGTH: 25
<212> TYPE: DNA
<213> ORGANISM: Artificial Sequence
<220> FEATURE:
<223> OTHER INFORMATION: Synthetic Construct

<400> SEQUENCE: 3
taaacttgac ctaaagacca ttgca                                          25

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
cagcaaaccg cttgggatta                                                20

<210> SEQ ID NO 5
<211> LENGTH: 100
<212> TYPE: DNA
<213> ORGANISM: Artificial Sequence
<220> FEATURE:
<223> OTHER INFORMATION: Synthetic Construct

<400> SEQUENCE: 5
tactgcatcc acaacattac tggcgtgctt tttgctttgc ttttgtgtgc ttttgtgtgt    60
ctgcctatta atacgtccgc tgcttttgtc tgtgtctaca                          100

<210> SEQ ID NO 6
<211> LENGTH: 100
<212> TYPE: DNA
<213> ORGANISM: Artificial Sequence
<220> FEATURE:
<223> OTHER INFORMATION: Synthetic Construct

<400> SEQUENCE: 6
gaatgtgtgt actgcaagca acagttactg cgacgtgagg tatatgactt tgcttttcgg    60
gatttatgca tagtatatag agatgggaat ccatatgctg                          100
```